United States Patent
Volobuev et al.

(10) Patent No.: US 11,903,811 B2
(45) Date of Patent: *Feb. 20, 2024

(54) EMBOLUS BLOOD CLOT FILTER REMOVAL SYSTEM AND METHOD

(71) Applicant: C.R. BARD, INC., Murray Hill, NJ (US)

(72) Inventors: Dmitry Mikhailovich Volobuev, St. Petersburg (RU); Alexander Germanovich Kashkarov, St. Petersburg (RU); Andrzej J. Chanduszko, Chandler, AZ (US)

(73) Assignee: C.R. BARD, INC., Murray Hill, NJ (US)

( * ) Notice: Subject to any disclaimer, the term of this patent is extended or adjusted under 35 U.S.C. 154(b) by 353 days.

This patent is subject to a terminal disclaimer.

(21) Appl. No.: 17/324,656

(22) Filed: May 19, 2021

(65) Prior Publication Data

US 2021/0338407 A1 Nov. 4, 2021

Related U.S. Application Data

(63) Continuation of application No. 15/660,646, filed on Jul. 26, 2017, now Pat. No. 11,039,913, which is a (Continued)

(51) Int. Cl.
*A61F 2/01* (2006.01)
*A61B 17/221* (2006.01)

(52) U.S. Cl.
CPC ............ *A61F 2/011* (2020.05); *A61B 17/221* (2013.01); *A61F 2/01* (2013.01); *A61F 2/0105* (2020.05);
(Continued)

(58) Field of Classification Search
CPC .......... A61F 2/011; A61F 2/01; A61F 2/0105; A61F 2230/005; A61F 2230/0067;
(Continued)

(56) References Cited

U.S. PATENT DOCUMENTS 4,425,908 A 1/1984 Simon
4,471,777 A 9/1984 McCorkle, Jr.
(Continued)

FOREIGN PATENT DOCUMENTS

EP 188927 B1 7/1989
WO 0056231 A1 9/2000
(Continued)

OTHER PUBLICATIONS

Extended European Search Report, dated Sep. 26, 2012, for European Application No. 06846868.5 corresponding to PCT/US2006/062733.

*Primary Examiner* — Richard G Louis
(74) *Attorney, Agent, or Firm* — Garvey, Smith & Nehrbass, Patent Attorneys, L.L.C.; Charles C. Garvey, Jr.; Fabian M. Nehrbass

(57) ABSTRACT

A blood filter extraction system for extracting a blood filter from within a blood vessel. The system includes an extraction wire, or plurality of such wires, positioned within an elongated tubular member. A plurality of extraction wires coupled to the distal end of the extraction member each include a hook for engaging filter members. Alternatively, the extraction wires may be one or more wires configured in a helical shape which engage filter members when the extraction member is rotated. The system may also include an elongated tubular member with the distal end having a conical shape. To extract a filter, the extraction wires are then pushed out of the tubular member and into the filter members. The extraction member is then withdrawn or rotated so the wires engage and draw in the filter members,
(Continued)

after which the catheter is pushed over the conical portion of the tubular member.

15 Claims, 18 Drawing Sheets

Related U.S. Application Data continuation of application No. 12/096,367, filed as application No. PCT/US2006/062733 on Dec. 29, 2006, now Pat. No. 9,730,781.

(60) Provisional application No. 60/754,598, filed on Dec. 30, 2005.

(52) U.S. Cl.
CPC . *A61B 2017/2215* (2013.01); *A61F 2002/016* (2013.01); *A61F 2230/005* (2013.01); *A61F 2230/008* (2013.01); *A61F 2230/0067* (2013.01); *A61F 2250/0059* (2013.01)

(58) Field of Classification Search
CPC ....... A61F 2230/008; A61F 2250/0059; A61B 17/221; A61B 2017/2215; A61B 2002/016
See application file for complete search history.

(56) References Cited

U.S. PATENT DOCUMENTS

| | | | |
|---|---|---|---|
| 4,494,531 A | 1/1985 | Gianturco | |
| 4,611,594 A | 9/1986 | Grayhack et al. | |
| 4,688,553 A | 8/1987 | Metals | |
| 5,108,418 A | 4/1992 | Lefebvre | |
| 5,669,933 A | 9/1997 | Simon et al. | |
| 5,709,704 A | 1/1998 | Nott et al. | |
| 5,776,162 A | 7/1998 | Kleshinski | |
| 5,800,457 A | 9/1998 | Gelbfish | |
| 5,836,968 A | 11/1998 | Simon et al. | |
| 5,850,455 A | 12/1998 | Arnold et al. | |
| 6,007,558 A | 12/1999 | Ravenscroft et al. | |
| 6,080,178 A | 6/2000 | Meglin | |
| 6,152,946 A | 11/2000 | Broome et al. | |
| 6,156,055 A | 12/2000 | Ravenscroft | |
| 6,176,871 B1 | 1/2001 | Pathak et al. | |
| 6,193,739 B1 | 2/2001 | Chevillon et al. | |
| 6,241,738 B1 | 6/2001 | Dereume | |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,331,183 B1 | 12/2001 | Suon | |
| 6,436,120 B1 | 8/2002 | Meglin | |
| 6,443,972 B1 | 9/2002 | Bosma et al. | |
| 6,454,775 B1 | 9/2002 | Demarais et al. | |
| 6,468,290 B1 | 10/2002 | Weldon et al. | |
| 6,540,767 B1 | 4/2003 | Walak et al. | |
| 6,569,181 B1 | 5/2003 | Burns | |
| 6,575,995 B1 | 6/2003 | Huter et al. | |
| 6,589,266 B2 | 7/2003 | Whitcher et al. | |
| 6,623,506 B2 | 9/2003 | McGuckin, Jr. et al. | |
| 6,846,317 B1 * | 1/2005 | Nigon ................. | A61B 17/221 606/200 |
| 6,872,217 B2 | 3/2005 | Walak et al. | |
| 7,056,286 B2 | 6/2006 | Ravenscroft et al. | |
| 7,776,052 B2 | 8/2010 | Greenberg et al. | |
| 2001/0003796 A1 | 6/2001 | Yang et al. | |
| 2001/0039432 A1 | 11/2001 | Whitcher et al. | |
| 2002/0107526 A1 | 8/2002 | Greenberg et al. | |
| 2002/0133191 A1 | 9/2002 | Khosravi et al. | |
| 2003/0071285 A1 | 4/2003 | Tsukernik | |
| 2003/0074019 A1 | 4/2003 | Gray et al. | |
| 2003/0114879 A1 | 6/2003 | Euteneuer et al. | |
| 2003/0187495 A1 | 10/2003 | Cully et al. | |
| 2003/0212429 A1 | 11/2003 | Keegan et al. | |
| 2004/0073243 A1 | 4/2004 | Sepetka et al. | |
| 2004/0073252 A1 | 4/2004 | Goldberg et al. | |
| 2004/0186512 A1 | 9/2004 | Bruckheimer et al. | |
| 2004/0193209 A1 | 9/2004 | Pavcnik et al. | |
| 2005/0055045 A1 | 3/2005 | DeVries et al. | |
| 2005/0085847 A1 | 4/2005 | Galdonik et al. | |
| 2005/0159771 A1 | 7/2005 | Petersen | |
| 2005/0159773 A1 | 7/2005 | Broome et al. | |
| 2005/0163821 A1 | 7/2005 | Sung et al. | |
| 2005/0177224 A1 | 8/2005 | Fogarty et al. | |
| 2005/0234503 A1 | 10/2005 | Ravenscroft et al. | |
| 2005/0277977 A1 | 12/2005 | Thornton | |
| 2006/0036279 A1 | 2/2006 | Eidenschink et al. | |
| 2006/0069405 A1 | 3/2006 | Schaeffer et al. | |
| 2006/0095068 A1 | 5/2006 | WasDyke et al. | |
| 2006/0184193 A1 * | 8/2006 | Lowe ................... | A61F 2/0103 606/200 |
| 2006/0247572 A1 | 11/2006 | McCartney | |
| 2006/0287668 A1 | 12/2006 | Fawzi et al. | |

FOREIGN PATENT DOCUMENTS

| | | |
|---|---|---|
| WO | 03022325 A2 | 3/2003 |
| WO | 3022325 A3 | 3/2003 |
| WO | 03022325 A8 | 8/2003 |
| WO | 2006124405 A2 | 11/2006 |
| WO | 2007021340 A1 | 2/2007 |

* cited by examiner

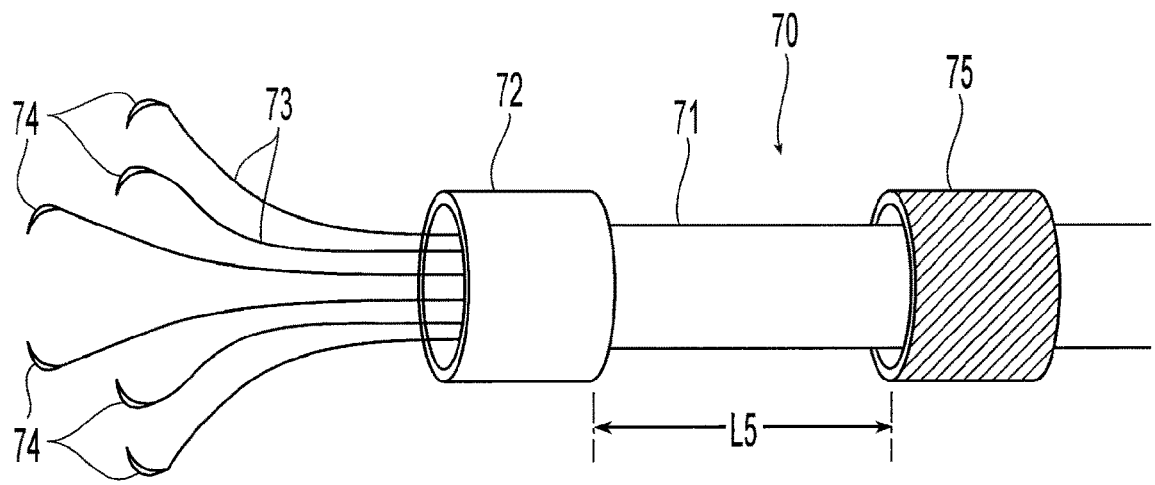
*Fig. 4*
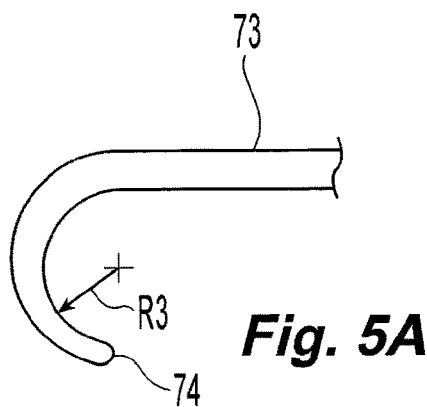
*Fig. 5A*
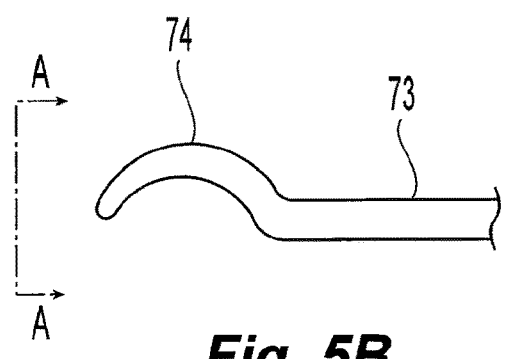
*Fig. 5B*
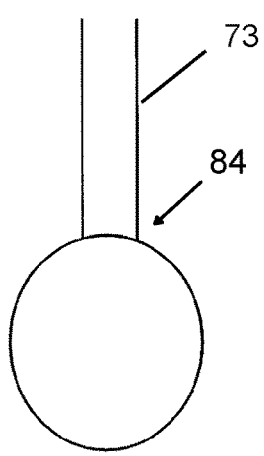
*Fig. 5D*
*Fig. 5C*
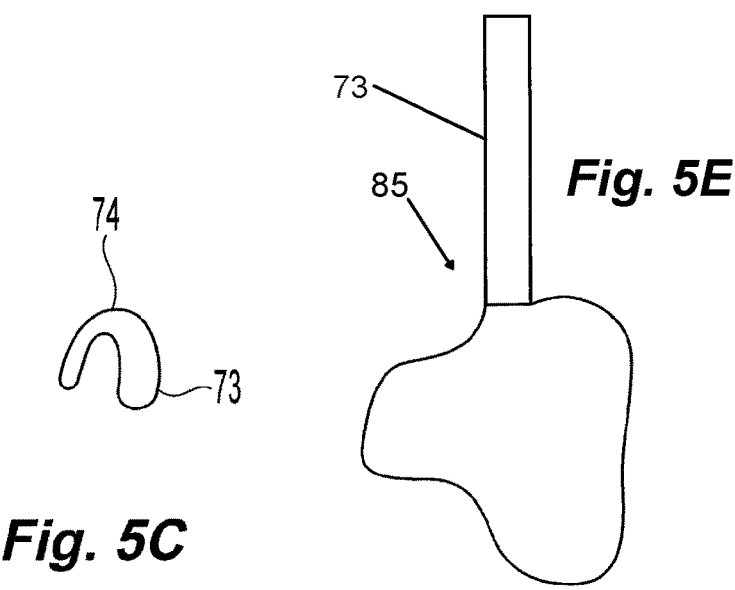
*Fig. 5E*

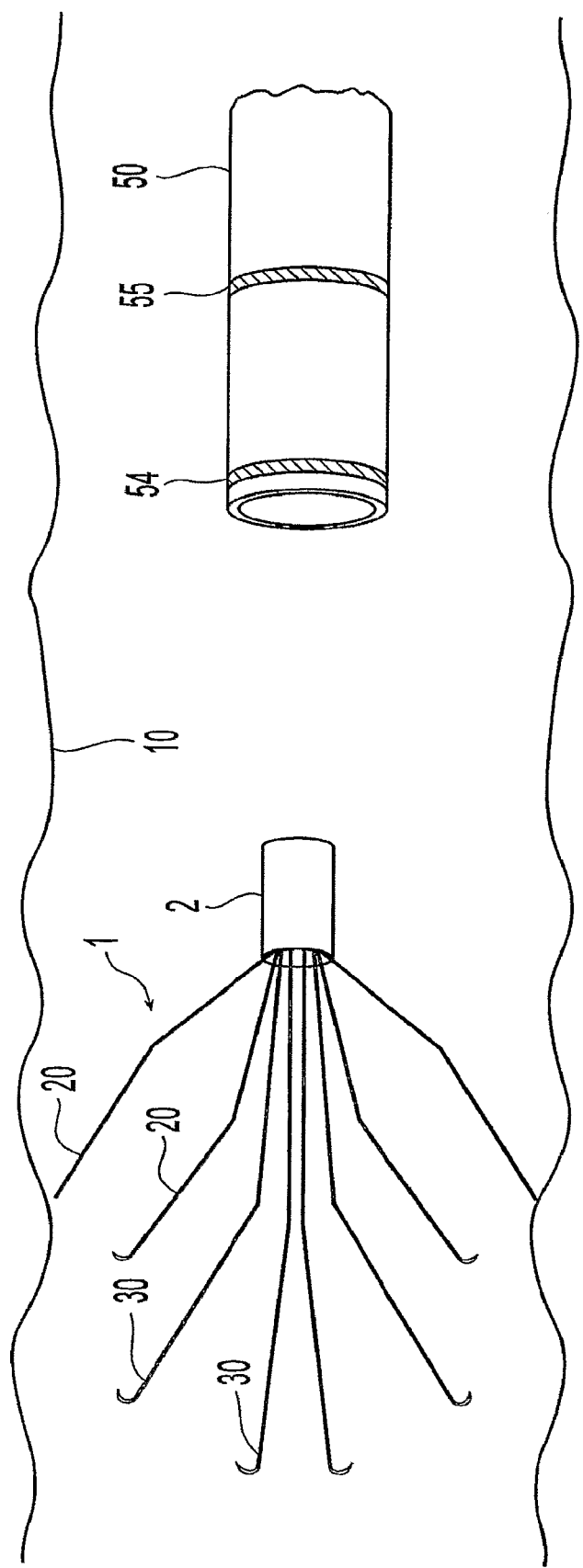

EMBOLUS BLOOD CLOT FILTER REMOVAL SYSTEM AND METHOD

PRIORITY DATA AND INCORPORATION BY REFERENCE

This is a continuation of U.S. patent application Ser. No. 15/660,646, filed Jul. 26, 2017 (now U.S. Pat. No. 11,039,913), which is a continuation of U.S. patent application Ser. No. 12/096,367, filed Sep. 9, 2008 (now U.S. Pat. No. 9,730,781), which is a National Stage application under 35 U.S.C. 371 of International Application No. PCT/US2006/062733, filed Dec. 29, 2006, which claims the benefit of priority to U.S. Provisional Patent Application No. 60/754,598, filed Dec. 30, 2005 which is incorporated by reference in its entirety. This invention is related to the subject matter shown and described in the following: (i) PCT International Application No. PCT/US06/62722, filed Dec. 29, 2006, entitled "Removable Blood Clot Filter with Edge For Cutting Through the Endothelium" and claiming the benefit of priority to U.S. Provisional Patent Application No. 60/754,600, filed Dec. 30, 2005; (ii) PCT International Application No. PCT/US06/62719, filed Dec. 29, 2006, entitled "Embolus Blood Clot Filter with Post Delivery Actuation," and claiming the benefit of priority to U.S. Provisional Patent Application No. 60/754,633, filed Dec. 30, 2005; (iii) PCT International Application No. PCT/US06/62725 filed Dec. 29, 2006, entitled "Embolus Blood Clot Filter Delivery System," and claiming the benefit of priority to U.S. Provisional Patent Application No. 60/754,636, filed Dec. 30, 2005; (iv) PCT International Application No. PCT/US06/62720, filed Dec. 29, 2006, entitled "Embolus Blood Clot Filter with Floating Filter Basket," and claiming the benefit of priority to U.S. Provisional Patent Application No. 60/754,599, filed Dec. 30, 2005; and (v) PCT International Application No. PCT/US06/62730 filed Dec. 29, 2006, entitled "Embolus Blood Clot Filter with Bio-Resorbable Coated Filter Members," and claiming the benefit of priority to U.S. Provisional Patent Application No. 60/754,597, entitled "Embolus Blood Clot Filter with Retainers on Locator Filter Members," filed Dec. 30, 2005, each of which is hereby incorporated by reference in its entirety.

TECHNICAL FIELD

This invention relates to a medical apparatus for removing filter devices from a vessel of a mammalian body, and more particularly for a catheter-born blood filter extraction apparatus and methods of using it.

BACKGROUND ART

In recent years, a number of medical devices have been designed which are adapted for compression into a small size to facilitate introduction into a vascular passageway and which are subsequently expandable into contact with the walls of the passageway. These devices include, among others, blood clot filters which expand and are held in position by engagement with the inner wall of a vein, such as the vena cava. Vena cava filters are known in the art as described, for example, in U.S. Pat. Nos. 4,425,908, 5,669,933 and 5,836,968 and European Patent Office publication 0 188 927 A2, which are hereby incorporated by reference in their entireties. These vena cava filters are generally designed to remain in place permanently. Such filters include structure to anchor the filter within the vena cava, such as elongate diverging anchor members with hooked ends that penetrate the vessel wall and positively prevent longitudinal migration in either direction within the vessel. The hooks on filters of this type are rigid and will not bend, and within two to six weeks after a filter of this type has been implanted, the endothelium layer grows over the diverging anchor members and positively locks the hooks in place. Any attempt to remove the filter thereafter risks injury to or rupture of the vena cava. Nevertheless, a number of vena cava filters have been fitted with a hook on the hub that can be snared and used to pull the filter into a catheter for removal, an example of which is disclosed in U.S. Pat. No. 5,836,968, which is hereby incorporated by reference in its entirety.

Most existing filters, including filters currently present in patients, are not configured to be removable or fitted with an extraction hook and their configurations render them difficult or potentially dangerous to remove. In addition to the challenge of disengaging the filter members from the endothelium without rupturing the blood vessel, there is the difficulty of locating and acquiring the filter so that it can be withdrawn from the vessel into an intravenal catheter. Accordingly, there is a need for an apparatus that can safely locate, capture and remove a blood filter from a patient without the need for major surgery.

DISCLOSURE OF INVENTION

An apparatus for removing a blood filter from a blood vessel includes an elongate extraction member configured to be positioned within the lumen of a catheter and to move longitudinally and rotationally with respect to the catheter. The extraction member includes a plurality of wires coupled to its distal end with a hook coupled to each of the plurality of wires. The extraction member may be positioned within an elongated tubular member, which includes a conical portion on the distal end. Alternatively, a conical portion may be coupled to the extraction member.

Another embodiment of an apparatus for removing a blood filter from a blood vessel includes an elongated extraction member configured to be positioned within the lumen of a catheter and to move longitudinally and rotationally with respect to the catheter. The elongated extraction member preferably includes a first extraction wire coupled to its distal end. The first extraction wire may be configured as a helix and coupled to the distal end of the elongated extraction member. The extraction member may also include a second helical extraction wire coupled to the distal end of the extraction member.

A method for removing a filter from a blood vessel having a plurality of filter members including at least some of the steps of positioning a catheter in the blood vessel so a distal end of the catheter is proximal to the filter; inserting a tubular member into the catheter; positioning the tubular member in the catheter so the conical member extends from the distal end of the catheter and passes over a portion of the filter; inserting an extraction member into the tubular member, the extraction member includes a plurality of wires each of which includes a hook; pushing the extraction member within the tubular member in a distal direction until the plurality of wires extend beyond the distal end of the catheter and contact the filter members; pulling the extraction member in a proximal direction while not moving the catheter or the tubular member such that the filter members move toward the centerline; positioning the tubular member so the conical member contacts a portion of the filter; pushing the catheter in a distal direction without moving the tubular member to cause the catheter to collapse the conical member over at least a portion of the filter; drawing the filter and tubular member into the catheter; and removing the catheter from the patient.

A method for removing a filter from a blood vessel having a plurality of filter members including at least some of the steps of positioning a catheter in the blood vessel so a distal end of the catheter is proximal to the filter; inserting an extraction member into the tubular member, the extraction member including a helical extraction wire on the distal end; positioning the helical extraction wire over a portion of the filter; rotating the extraction member to cause the helical extraction wire to engage filter; drawing the filter into the catheter; and removing the catheter from the patient.

BRIEF DESCRIPTION OF THE DRAWINGS

The accompanying drawings, which are incorporated herein and constitute part of this specification, illustrate various embodiments of the invention, and, together with the general description given above and the detailed description given below, explain features of the invention.

FIG. 4 is a side perspective of a filter extraction member that preferably forms part of an embodiment filter extraction system.

FIG. 5A through 5E are detail perspective views of hooking or snaring elements of the extraction member illustrated in FIG. 4.

FIG. 8 illustrates the positioning of the catheter shown in FIG. 2 near a filter within a blood vessel.

MODE(S) FOR CARRYING OUT THE INVENTION

The accompanying drawings and description represent the preferred embodiments of the invention. Wherever possible, the same reference numbers will be used throughout the drawings to refer to the same or like parts.

As used herein, the terms "about" or "approximately" for any numerical values or ranges indicate a suitable dimensional tolerance that allows the part or collection of components to function for its intended purpose as described herein. Also, as used herein, the terms "patient," "host" and "subject" refer to any human or animal subject and are not intended to limit the systems or methods to human use, although use of the subject invention in a human patient represents a preferred embodiment. Moreover, as used herein, the term "wire" refers to any elongated member of narrow cross section, including rods, bars, tubes, ribbon and narrow sections cut from thin plate, and is not intended to limit the scope of the invention to elongated members of circular cross section, cut from wire stock or manufactured according to a particular method of metal forming.

Figure 1:
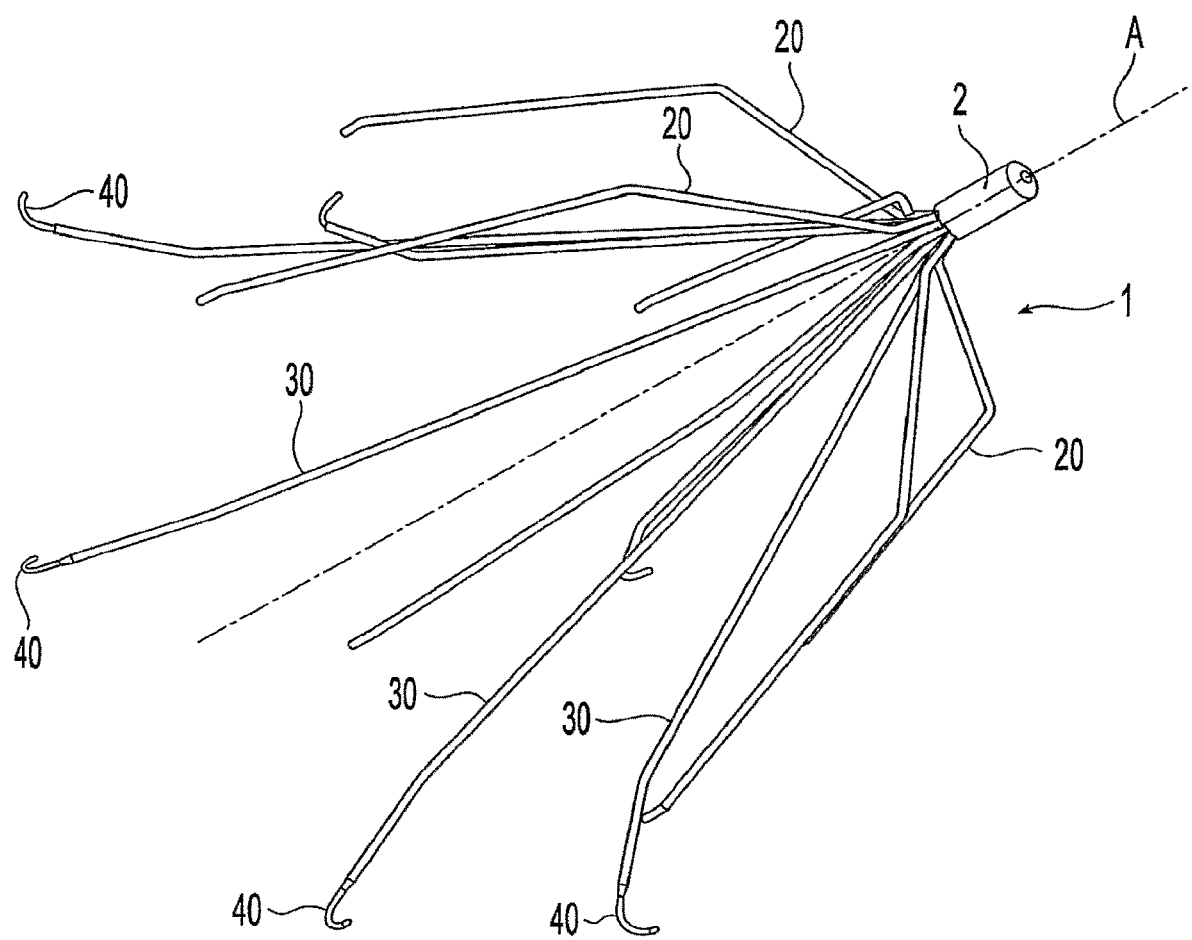
FIG. 1 is a perspective view of a blood filter.

The various embodiments of the blood filter extraction system are configured to engage and retract a typical blood filter from within a patient's blood vessel, such as the vena cava. A preferred blood filter 1 is illustrated in FIG. 1. Typically, a blood filter includes a number of filter members (e.g., wires) which both position and anchor the filter within a blood vessel and serve as the filtering elements which catch and retain blood clots in the blood.

Referring to FIG. 1, a filter 1 may include a plurality of anchor members 30 which are positioned radially around the filter 1 and include hooks 40 which hook into the blood vessel wall to secure the filter within the vessel. A filter 1 may also include locator members 20 positioned radially around the filter and configured to press radially outward against the blood vessel wall to center the filter within the vessel. A filter 1 may also include a hub 2 to which the locator members 20 and anchor members 30 are attached, such as by welding. When deployed within a blood vessel, the anchor members 30 preferably form a first conical filter basket while the locator members 20 further preferably form a second filter basket positioned downstream from the first filter basket. The hooks 40 may be configured to have a reduced cross section compared to the rest of the anchor or locator members. By reducing the cross sectional area of a portion or all of the hooks 40 relative to that of the anchor members 30 or locator members 20, stress will be concentrated in the areas of reduced cross section when longitudinal force is applied to the hub 2 in the direction of blood flow BF (i.e., towards the hub 2 of the filter) such as to remove the filter. Further description of blood filter configurations and constructions are provided in U.S. Pat. No. 6,258,026, and PCT International Application No. PCT/US06/017889, entitled "Removable Embolus Blood Clot Filter," filed May 9, 2006, both of which are hereby incorporated by reference in their entireties. Also, descriptions of systems and methods used for implanting a filter in a blood vessel are provided in PCT International Application No. PCT/US06/17890, entitled "Embolus Blood Clot Filter and Delivery System," filed on May 9, 2006, which is also hereby incorporated by reference in its entirety.

When a filter 1, such as that illustrated in FIG. 1, has been in place within a blood vessel for a few weeks, the endothelial layer will tend to grow over the portions of the anchors 30, in particular the hooks 40, and the locator members 20 in contact with the vessel wall. This endothelial overgrowth helps to hold the filter 1 in position, but may create difficulties for extraction procedures. To avoid this, it is preferable to depress the filter members 20, 30 (i.e., anchors and locators) toward the vessel centerline before the filter is moved longitudinally through the vessel. Accordingly, preferred embodiments of the blood filter extraction system first engage the filter members with an extraction wire and then radially collapse the filter members away from the vessel walls and into a catheter before the catheter is withdrawn from the blood vessel.

Figure 2:
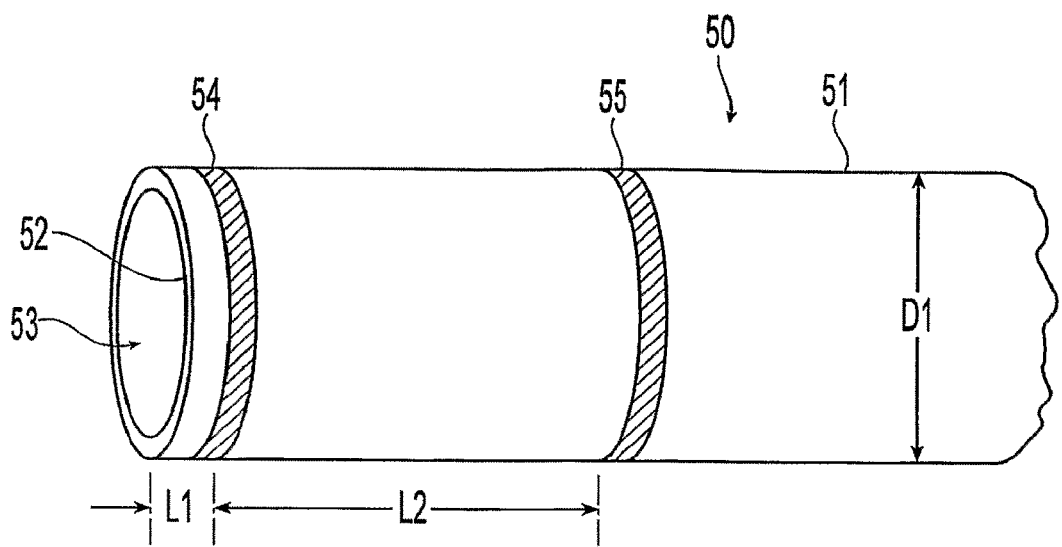
FIG. 2 is a side view of a catheter suitable for use with an embodiment filter extraction system.
Figure 13:
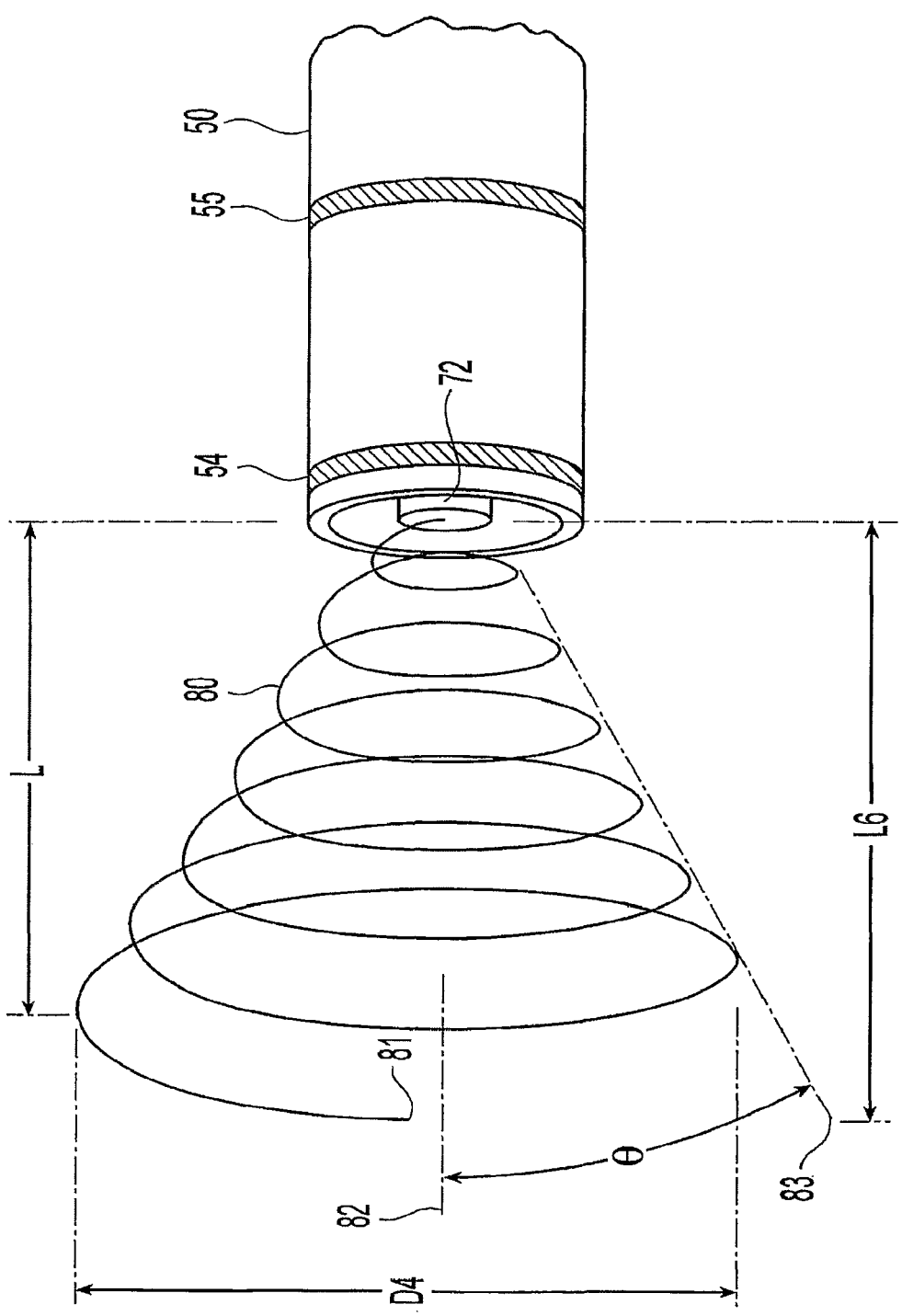
FIG. 13 is a side perspective of a filter extraction member of an alternative embodiment filter extraction system.
Figure 14:
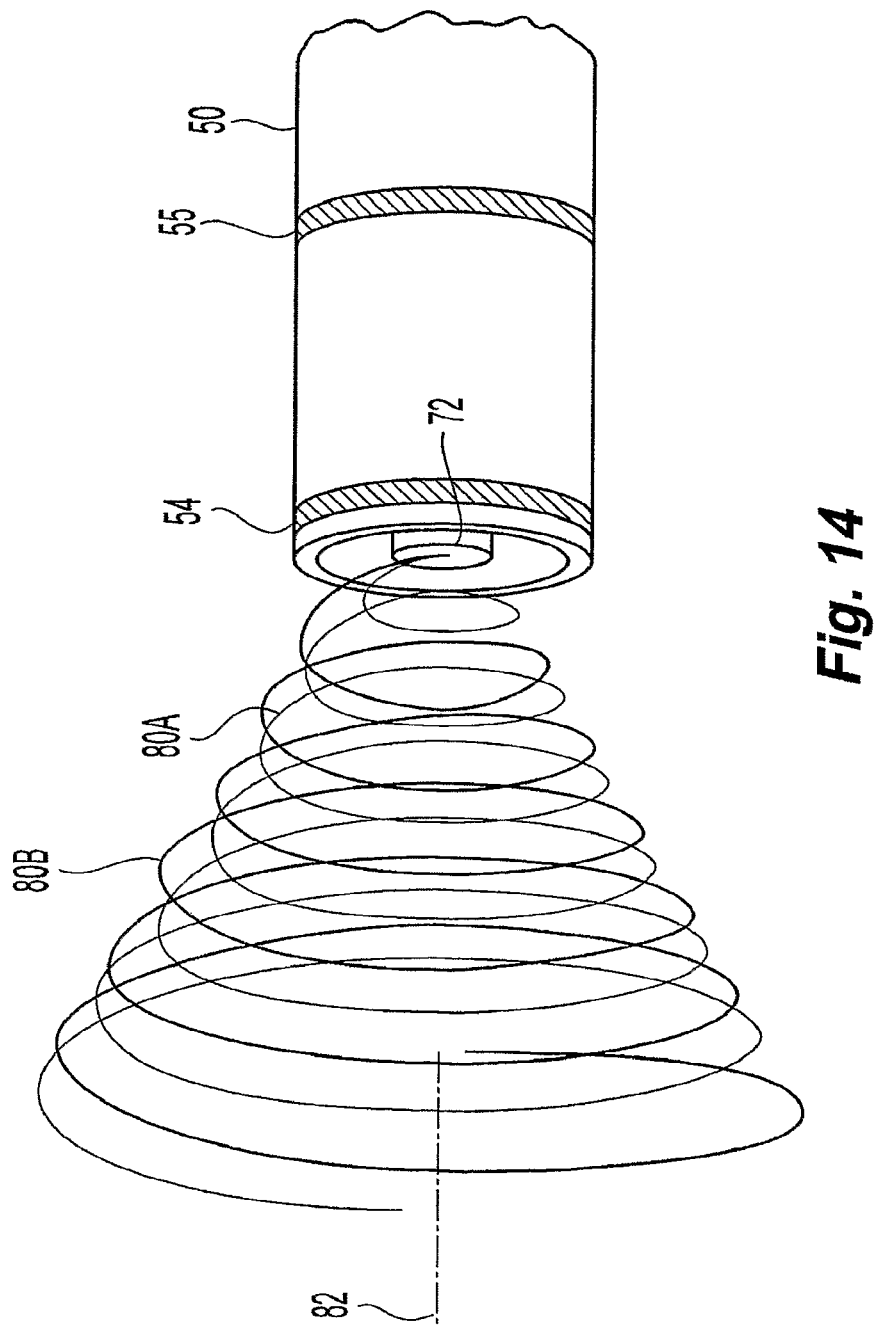
FIG. 14 is a side perspective of a filter extraction member of an alternative embodiment filter extraction system.

One preferred embodiment of the blood filter extraction system includes an extraction member (embodiments of which are illustrated in FIGS. 4, 13 and 14), which is preferably configured to be delivered to the vicinity of the filter 1 by a catheter 50 (illustrated in FIG. 2). In some embodiments, an elongated tubular member (illustrated in FIG. 3) featuring a conical distal end is also used to help collapse the filter members when the catheter is pressed over the conical end.

The filter extraction system uses a catheter to gain access to the filter within a vessel and withdraw it from the patient's body. A standard medical catheter of about 7 to 10 French diameter may be used. In an embodiment illustrated in FIG. 2, a catheter 50 is provided as part of the filter extraction system that includes elements which facilitate the filter extraction process. Referring to FIG. 2, the catheter 50 has a diameter D1 which may be that of a 7 to 10 French diameter catheter, though larger and smaller catheters may also be used. The catheter 50 features an exterior surface 51 and an internal surface 52 defining an internal lumen 53. The catheter 50 is preferably about 45 inches long, although longer and shorter catheters may be used depending upon the size of the patient, the location of the blood filter to be extracted and the particular point of entry into the body to be used.

The catheter 50 may also include one or more radio-opaque markers 54 and 55 that can be easily imaged by radiography or fluoroscopy to permit a clinician to accurately determine the position of the catheter within a patient's body. In the embodiment illustrated in FIG. 2, two radio-opaque markers 54 and 55 are used, the first circumferential marker 54 located close to the distal end of the catheter 50, at length L1 from the end, and a second circumferential marker 55 located length L2 from the first marker 54. In a preferred embodiment, length L1 ranges from approximately 0.01 inch to approximately 0.5 inch, and length L2 ranges from approximately 0.5 inch to approximately 2 inches. As used herein, a radio-opaque marker is any material that is identifiable to machine or human-readable radiographic equipment while the material is inside a mammal body, such as, by way of example but not by way of limitation, gold, platinum, barium sulfate, or tantalum. The use of one marker allows a clinician to determine the location of a retrieving catheter tip. But two radio-opaque markers located a known distance apart can be utilized to allow the clinician to locate a delivery catheter within a blood vessel of the patient and accurately estimate the distance between the catheter's distal end and a filter. For example, the distance L2 between the first 54 and second 55 markers can be used as a distance scale when the filter and catheter are both imaged by fluoroscopy. To facilitate locating the catheter near the filter, the filter hub 2 can include a radio-opaque marker, such as by including a radio-opaque element in the hub material or coupling a radio-opaque marker to or within the hub 2.

In use, the catheter 50 may be introduced into a patient via an incision into a major vein, such as the jugular vein, or artery, such as the femoral artery, and advanced through the blood vessel 10 to the vicinity of the filter 1, as illustrated in FIG. 8. As mentioned above, the clinician may use fluoroscopy to confirm that the catheter 50 is positioned at a proper distance away from the filter 1. In this position, a clinician may advance an ultrasound imager (not shown) or a fiber optic imager (not shown) through the catheter 50 to inspect the filter to determine if extraction is required or to inspect the filter in preparation for extraction. Saline solution may be provided through the catheter 50 to displace blood in order to facilitate imaging by a fiber optic imager.

The catheter may be formed of any materials used for medical catheters, including by way of example polyurethane, polyethylene, polyamide, polyether block amide (PEBA), nylon, and combinations thereof.

Figure 3:
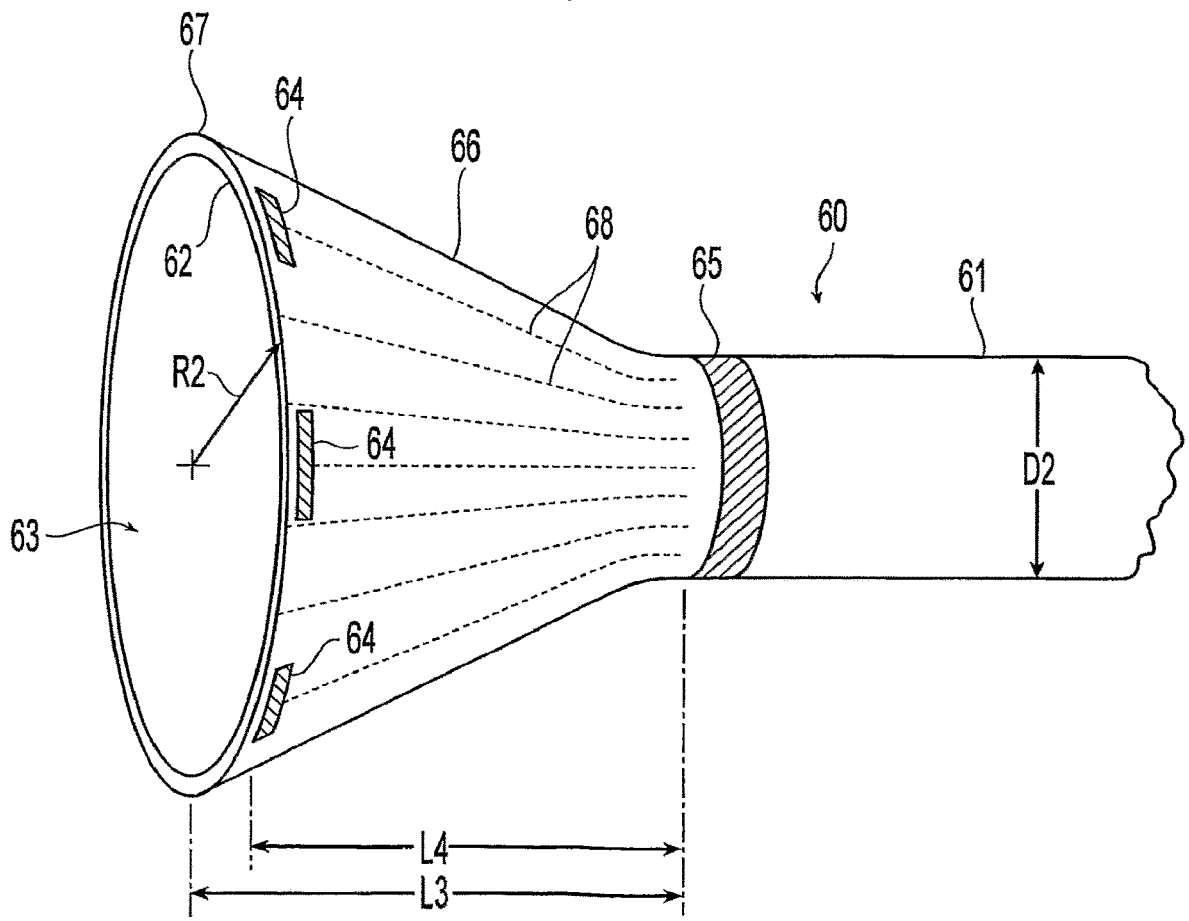
FIG. 3 is a side perspective view of a tubular member that preferably forms part of an embodiment filter extraction system.

In an embodiment illustrated in FIG. 3, an elongated tubular member 60 may be advanced through the catheter 50 to the vicinity of the filter. Alternatively, the elongated tubular member 60 may be positioned within the catheter 50 when the catheter is introduced into the patient. The tubular member 60 has a diameter D2, which is preferably slightly smaller than the internal diameter of the catheter 50 in which it is to be inserted. The tubular member 60 has an exterior surface 61 and an interior surface 62 defining an internal lumen 63, and a conical portion 66 defined by a radius R2 at the distal end 67. The tubular member 60 is preferably longer than the catheter 50 so that it can be manipulated by the clinician from the proximal end extending out of the catheter 50. In an embodiment, the tubular member may include radio-opaque markers 64, 65, located, for example, near the distal end 67 (markers 64) and a distance L3 from the distal end 67 (markers 65). The radio-opaque markers 64, 65 may be separated by a known distance L4 to facilitate determining the position of the conical end 66 with respect to the filter using fluoroscopy. In various embodiments, the radius R2 may range from approximately 0.25 inches to approximately 0.75 inches, the distance L4 may range from between approximately 0.01 inch and approximately 0.25 inch, and distance L3 may range from between approximately 0.5 inch and approximately 2 inches.

In order to permit the conical portion 66 to fit within the catheter 50, the tubular member 60 may include folds 68, which may be strips or zones of reduced thickness, along which the conical portion 66 preferentially folds or collapses. Radio-opaque markers 64 near the distal end 67 may be provided in arc segments as illustrated so that when the conical portion 66 is positioned within the catheter 50 the portions form an approximately continuous circumferential marker.

The tubular member may be formed of any materials used for medical catheters, including by way of example polyurethane, polyethylene, polyamide, polyether block amide (PEBA), nylon, and combinations thereof.

FIG. 4 illustrates an embodiment of the extraction member 70. An extraction member 70 has a long wire or rod 71 which will be longer than the catheter 50 and the tubular member 60 so that it can be manipulated by a clinician when in place. A handle may be provided on a proximal end to facilitate manipulation of the extraction member 70 by a clinician. A transition plug or hub 72 may be positioned at or near the distal end of the extraction member rod 71. This plug or hub 72 is coupled, such as by welding, brazing or swaging, to a plurality of extraction wires 73 extending therefrom in a distal direction. Each of the plurality of wires 73 may be tipped with a coupler 74 which is further preferably configured as a bend, loop or hook. The plurality of wires 73 may be of the same or different lengths preferably ranging from approximately 0.5 inch to approximately 1.5 inch, and may be configured to bend away from the centerline of the extraction member 70 in a conical fashion, when unconstrained. In order to permit imaging of the extraction member by fluoroscopy, the plug or hub 72 may include or be made of a radio-opaque material. To further aid in locating the extraction member 70 within a patient by fluoroscopy, a second (or more) radio-opaque marker 75 may be separated by a known distance L5. In an embodiment, the distance L5 between approximately 0.5 inches and approximately 2 inches.

It is noted that the plug or hub 72 can be a generally tubular member with a central lumen to allow for passage of a guidewire, contrast agent, saline or other members to be delivered to the tips of the wires 73. The couplers 74 on the tips of the plurality of wires 73 may be configured to increase the probability that they snare the locator and anchor members of the blood filter. To accomplish this, the couplers may be configured as a hook having a radius R3 that is approximately 1 to 3 times the diameter of the filter member wires. Further, the hooks may be off center and/or canted at an angle to the centerline of the wires as illustrated in FIGS. 5A, 5B and 5C, to increase the probability that the hooks will snare one or more filter wires when positioned among the filter members. Additionally, while the couplers 74 are shown as different types of hooks in FIGS. 5A-5C, other forms of couplers can be used.

For example, the generally spheroidal member 84 shown in FIG. 5D can replace the hooks or other couplers where the outer diameter of the spheroidal member 84 is smaller than a gap between any two adjacent locators or anchors of the blood filter. With the spheroidal members 84, the withdrawal of the wires 73 will cause the spheroidal members to move towards the longitudinal axis and come into contact with each other while retaining the portions of the filter proximal of the spheroidal members. Moreover, another foreseeable form of the couplers can be a single loop type, e.g., a snaring hoop 85 shown in FIG. 5E, to capture the proximal portion (e.g., hub) of the filter and locate such portion in a volume defined by the retrieving cone.

The extraction member rod or wire 71 may be fabricated of a solid wire, bar or tube of a material, such as stainless steel, with a sufficiently high modulus of elasticity to permit the extraction member 70 to be pushed through the elongated tubular member 60 and/or the catheter 50 without kinking and to be rotated within the elongated tubular member 60 and/or the catheter 50 without twisting or kinking. The plurality of wires 73 may be made from a metal such as stainless steel, or more preferably a shape memory alloy such as, for example, Nitinol preferably having an austenite finish ($A_f$) temperature below body temperature. Wires 73 made from Nitinol may be annealed in the desired conical configuration to establish that configuration as the wires' memory shape. So formed, the Nitinol wires 73 may be folded into a form that will fit within the elongated tubular member 60 and/or catheter 50.

Figure 6:
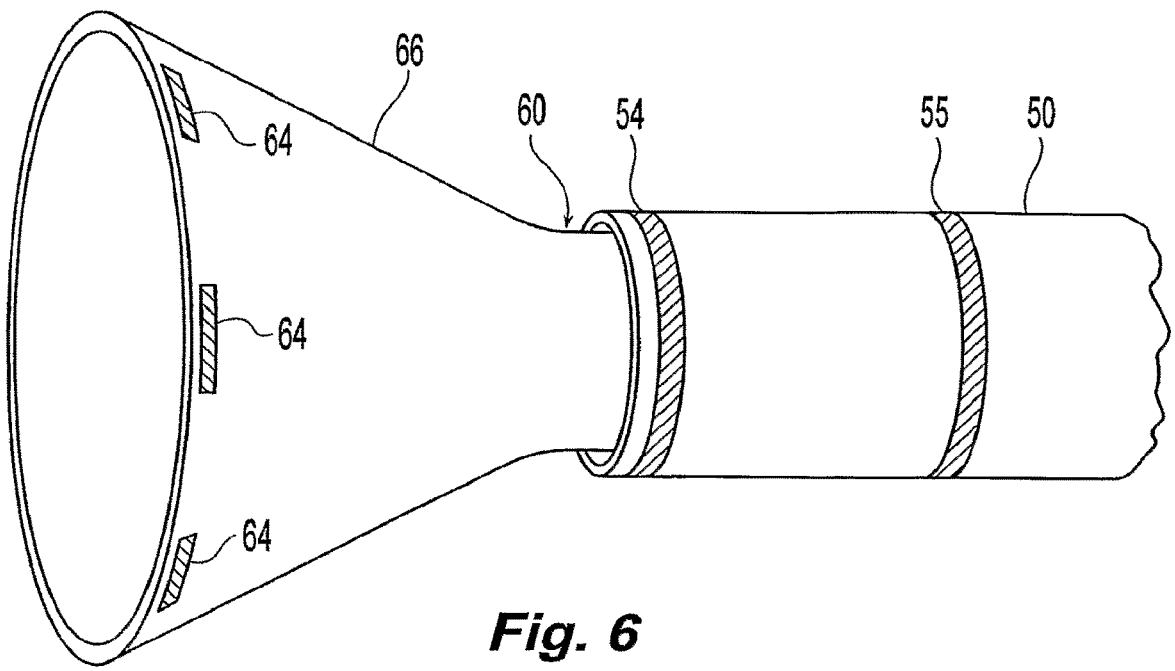
FIG. 6 is a side perspective view of an embodiment of the filter extraction system at a stage of deployment prior to engaging a filter.

In use, an embodiment of the elongated tubular member 60 may be advanced within the catheter 50 until the conical portion 66 extends beyond the distal end of the catheter 50, as illustrated in FIG. 6. Thus projecting from the catheter allows the conical portion 66 to be used to envelop the hub of a filter making it easier to engage the filter in a blood vessel. Also, the combination of radio-opaque markers on the conical portion (marker 64) and on the catheter (markers 54, 55) help a clinician to position the assembly near the filter using fluoroscopy. By comparing the distance between the radio-opaque markers 64 on the conical portion 66 and the catheter distal end radio-opaque marker 54 with the known distance between the radio-opaque markers 54, 55 on the catheter 50, the clinician can determine with fluoroscopy when the elongated tubular member 60 has been advanced sufficiently to allow full expansion of the conical portion 66 and/or when the conical portion 66 has encompassed the filter.

Figure 7A:
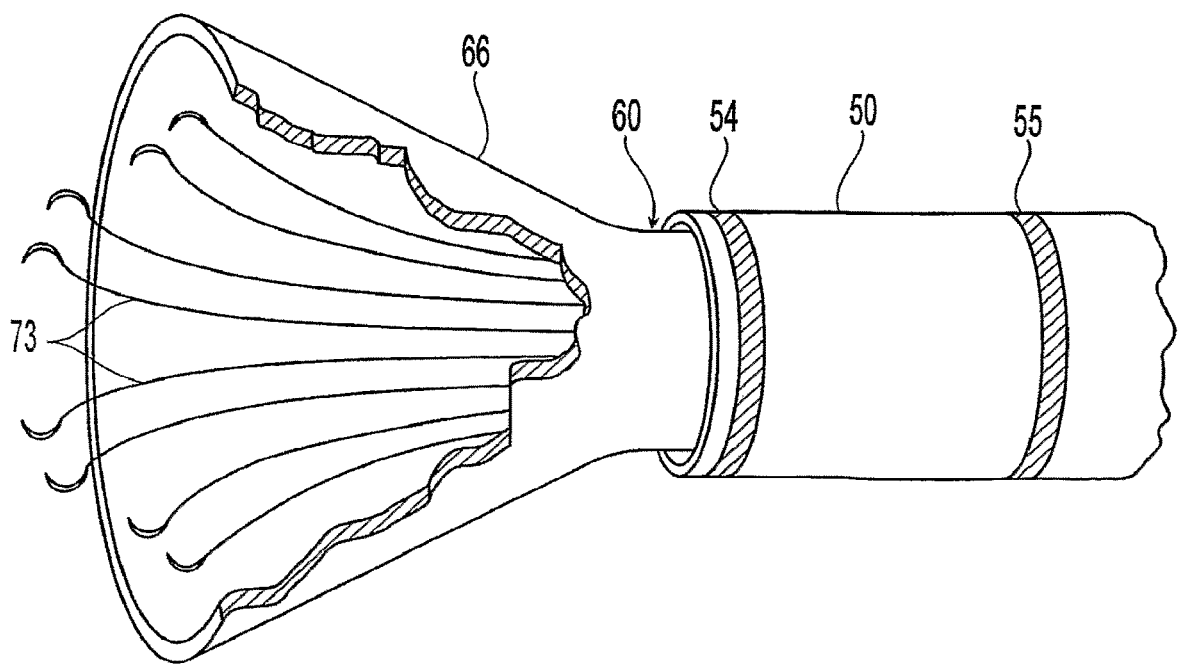
FIGS. 7A and 7B are side perspective views of an embodiment of the filter extraction system at later stages of deployment than that illustrated in FIG. 6.

In use, an embodiment of the extraction member 70 may be advanced within the elongated tubular member 60 so that the plurality of wires 73 extend within the conical member 66 as illustrated in FIG. 7A. In an alternative embodiment, the extraction member 70 may be advanced within the elongated tubular member 60 so that the plurality of extraction wires 73 extend beyond the conical member 66 as illustrated in FIG. 7B.

Figure 7B:
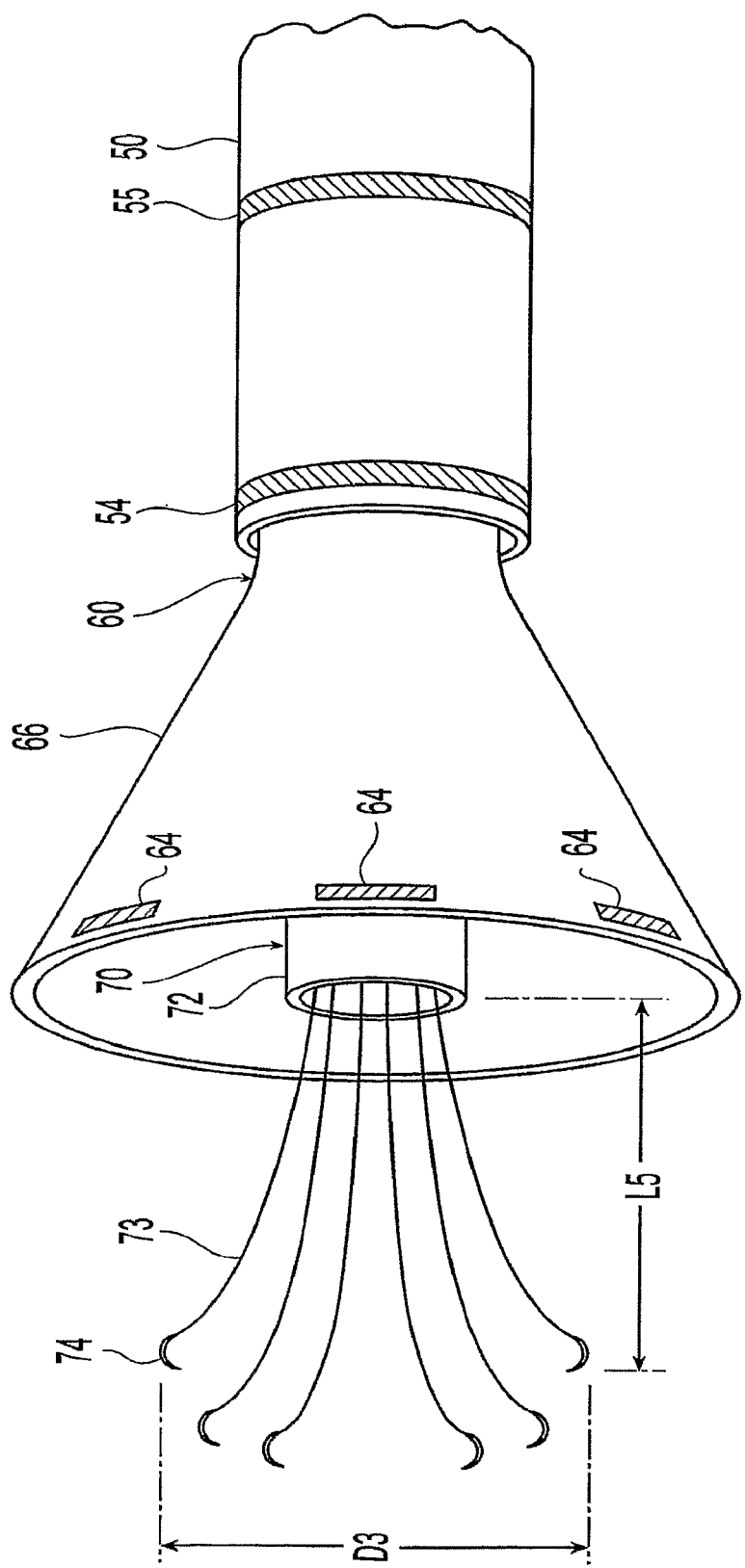

With the embodiments assembled in the configurations illustrated in FIGS. 7A and 7B, the filter extraction assembly is ready for engaging and extracting a filter. These configurations may be assembled through a number of alternative structural and/or methods of use embodiments. Examples of these alternative structure and assembly/use method embodiments are described below.

In one embodiment, the catheter 50 is first positioned near a filter in a blood vessel as illustrated in FIG. 8, the elongated tubular member 60 is next advanced through the catheter 50 until the conical portion 66 deploys as illustrated in FIG. 6, the extraction member 70 is then advanced through the elongated tubular member 60 until the plurality of wires 73 extends into the conical portion 66, as illustrated in FIG. 7A or beyond the conical portion 66, as illustrated in FIG. 7B. This embodiment of assembly permits a clinician to use the catheter 50 to inspect the filter prior to preparing to remove it.

In another embodiment, the extraction member 70 may be positioned within the elongated tubular member 60 during fabrication, so that in use, the clinician first positions the catheter 50 near a filter 1 in a vein as illustrated in FIG. 8, followed by advancing the pre-assembled elongated tubular member 60 and extraction member 70 through the catheter 50 until the conical portion 66 deploys as illustrated in FIGS. 6 and 7A. Finally, the extraction member 70 may be advanced a small distance to extend the plurality of wires 73 beyond the conical portion 66 as illustrated in FIG. 7B. This embodiment facilitates advancing the extraction member 70 within the catheter 50 since the plurality of wires 73 are enclosed within the conical portion 66 so they will not bind in the catheter.

In yet another embodiment, the extraction member 70 may be positioned within the elongated tubular member 60 which is positioned within the catheter 50 during fabrication as an extraction system. In this embodiment, the extraction member 70 and elongated tubular member 60 are initially positioned within the catheter 50. In use, the assembled extraction system is first advanced within a vein by the clinician until it is positioned near the filter. Then the tubular member 60 and extraction member 70 are distally advanced within the catheter 50 until the conical portion 66 extends as illustrated in FIGS. 6 and 7A. Finally, in an embodiment, the extraction member 70 may be distally advanced within the elongated tubular member 60 as illustrated in FIG. 7B.

Figure 9:
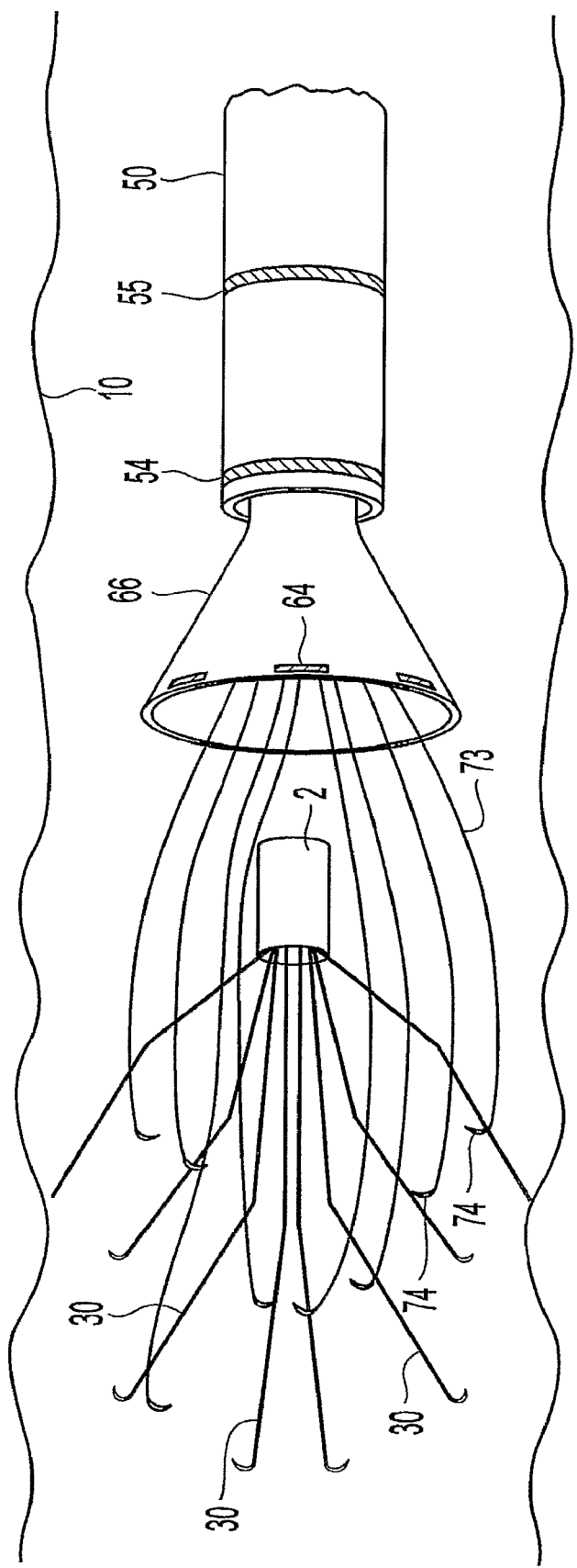
FIG. 9 illustrates a step in the process of extracting a blood filter from a blood vessel according to an embodiment.
Figure 10A:
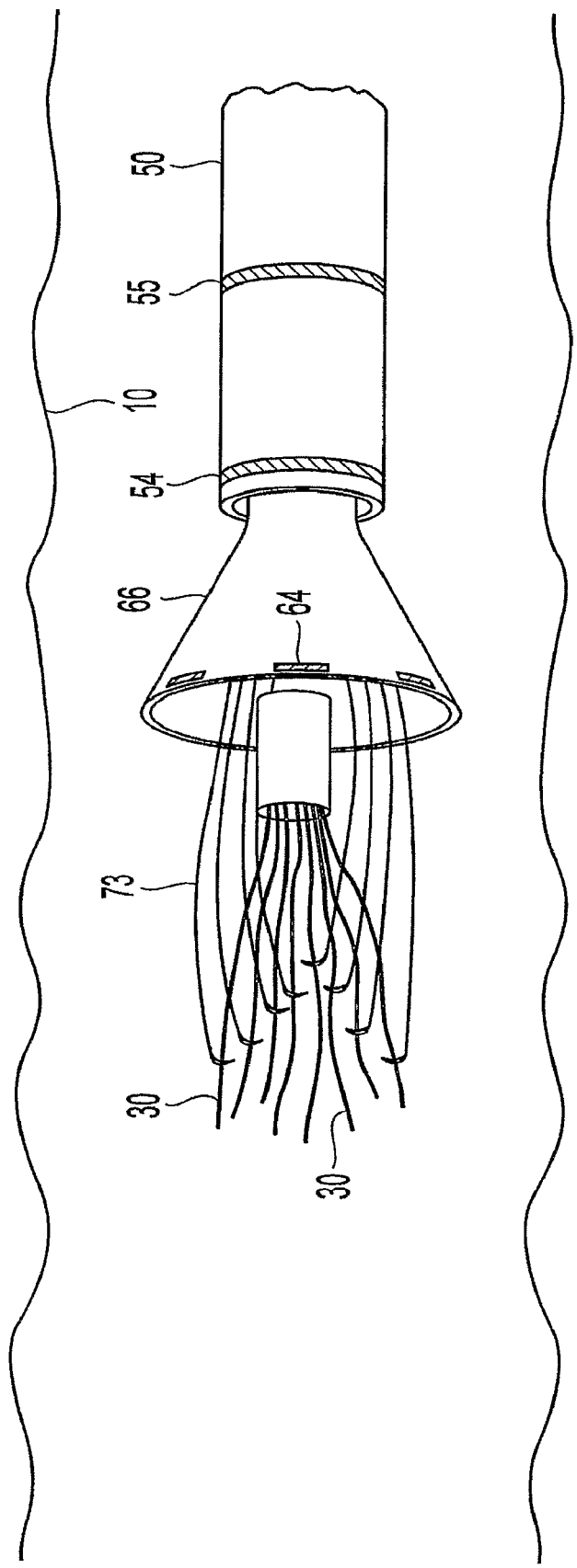
FIGS. 10A and 10B illustrate subsequent steps in the process of extracting a blood filter from a blood vessel according to an embodiment.
Figure 10B:
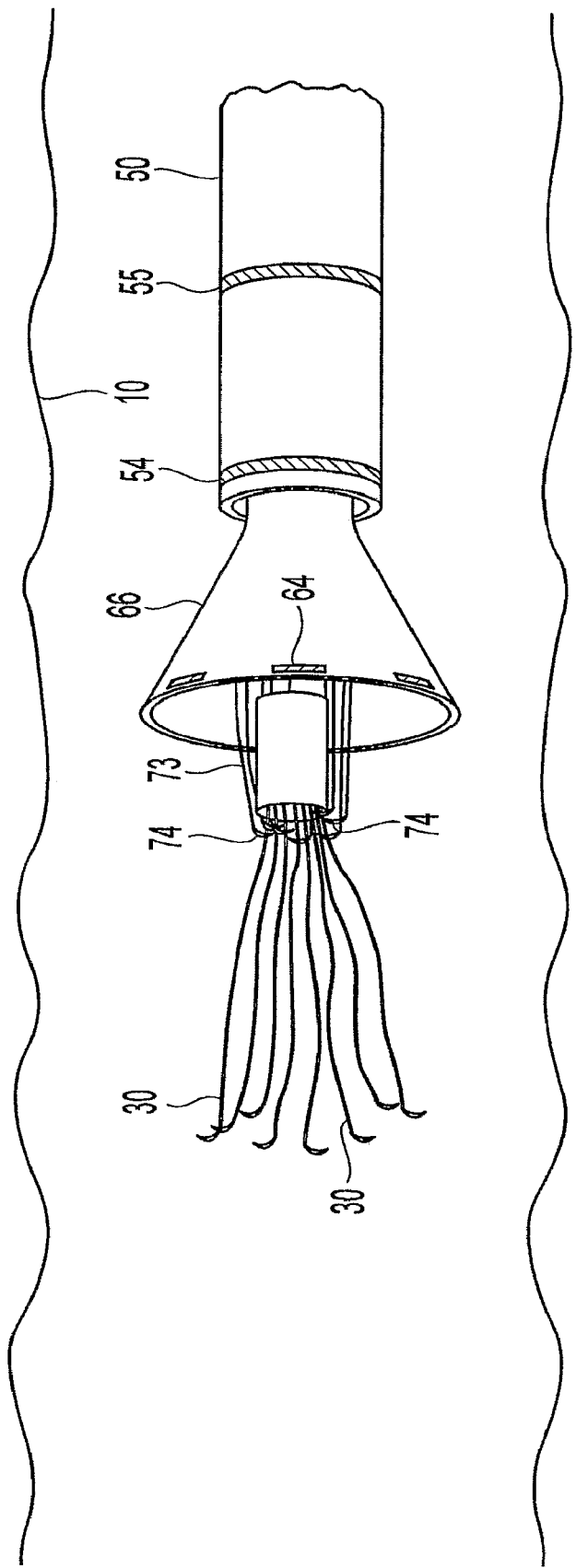
Figure 11A:
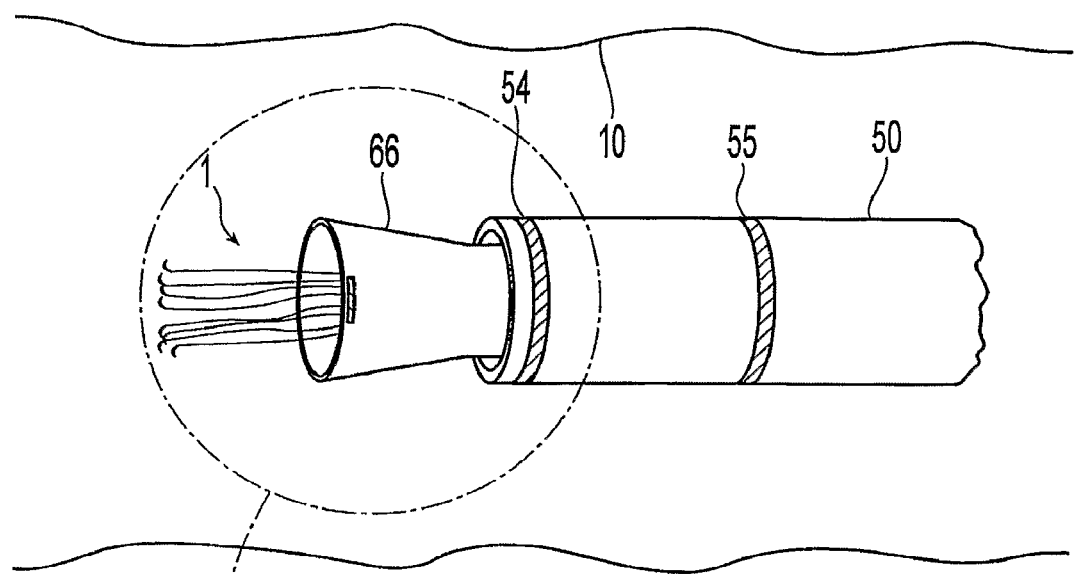
FIGS. 11A and 11B illustrate a further step in the process of extracting a blood filter from a blood vessel according to an embodiment.
Figure 11B:
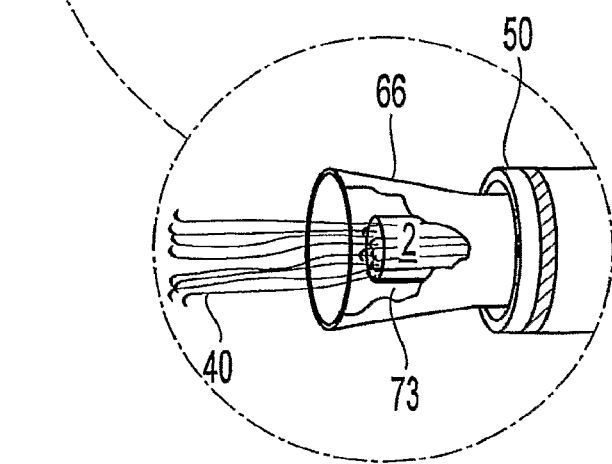
Figure 12:
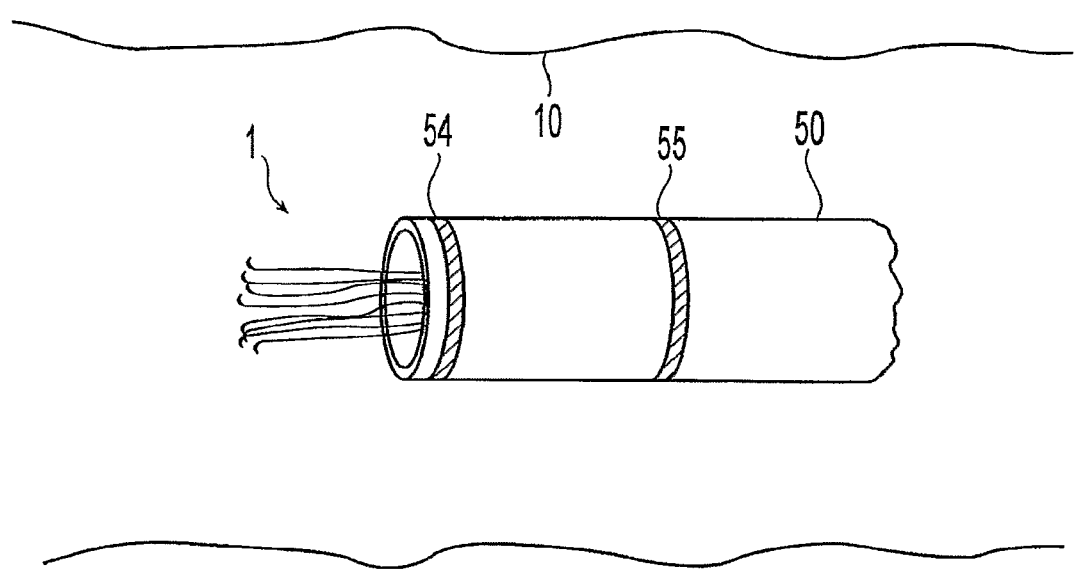
FIG. 12 illustrates a still further step in the process of extracting a blood filter from a blood vessel according to an embodiment.

Once the filter extraction assembly of one of the prior embodiments is deployed near the filter, the plurality of wires 73 are pressed into the filter members 20, 30 so the hooks on the wires can engage the filter locator and/or anchor members, as illustrated in FIGS. 9 and 10A. So engaged, the filter members can be pulled toward the centerline of the vessel and away from the wall by rotating the extraction member 70, as illustrated in FIG. 10B. Filter members 20, 30 can also be retracted by encompassing them within the conical portion 66 of the elongated tubular member 60. This may be accomplished by holding the extraction member 70 fixed while pushing the elongated tubular 60 member in a distal direction to position the conical portion 66 around the filter, including the filter members. To collapse the conical portion 66 over filter, the catheter 50 is pushed in the distal direction while holding the extended tubular member 60 and the extraction member 70 fixed. This is illustrated in FIGS. 11A and 11B. As the catheter 50 pushes over the conical member 66, the conical member 66 collapses inward pressing against the filter members 20, 30, further pulling the filter members away from the vessel wall. The conical portion 66 also covers the filter anchor hooks 40 so that they can be pulled into the catheter without catching on the vessel wall or the catheter. Finally, the filter 1 may be pulled fully into the catheter, as illustrated in FIG. 12, after which the catheter may be withdrawn from the patient's body.

An alternative embodiment of the filter extraction assembly is illustrated in FIGS. 13-18. In this embodiment, instead of a plurality of wires 73, one or a few extraction wires 80 coupled to the hub 72 are formed in a helical shape, preferably a conically shaped helix as illustrated in FIG. 13. When the helical extraction wire 80 is positioned over the filter, the extraction member 70 can be rotated in the direction of the helix, perhaps with some distal motion of the extraction member 70. As a result of this rotational motion, the helical extraction wire 80 encircles the filter members 20, 30 in a screw fashion, drawing the filter members in toward the centerline of the helix and toward the extraction member hub 72, thereby releasing the filter members from the blood vessel walls and securely attaching the helical extraction wire 80 to the filter.

In the embodiment illustrated in FIG. 13, the helical extraction wire 80 is formed in a conical shape with the narrow end of the cone coupled to the hub 72 of the extraction member 70. The conical helix shape may be characterized by its longitudinal extension length L6 between the hub 72 and the open distal end 81, its conical angle θ of the outside contour 83 to the centerline 82 of the helix and extraction member 70, and the number of rotations about the centerline 82 (i.e., density of the helix). This embodiment allows the extraction wire 80 to assist in positioning the extraction assembly over a filter since the broad open end 81 will engage the filter across an area larger than the cross section of the catheter. Rotation of the extraction wire 80 will draw the wire and the filter into centerline alignment. With further rotation, the helix and filter members 20, 30 become more tightly entangled, collapsing the extraction wire 80 about the filter so the captured filter can be drawn into the catheter 50.

In an alternative embodiment illustrated in FIG. 14, multiple helical extraction wires 80A, 80B are coupled to the hub 72 of the extraction member 70. FIG. 14 shows two helical extraction wires 80A and 80B, but three, four or more wires may be used. Preferably, the multiple helical wires are equiangularly offset about the centerline. For example, embodiments employing two helical wires will be rotationally oriented 180 degrees one from the other, and embodiments employing three helical wires may be rotationally oriented 120 degrees apart. Embodiments employing multiple helical wires 80 may more easily capture filter members since each rotation will pass more wires through the filter members 20, 30. Alternatively, the cross section of a single helical wire can be varied to achieve different stiffness.

Figure 15:
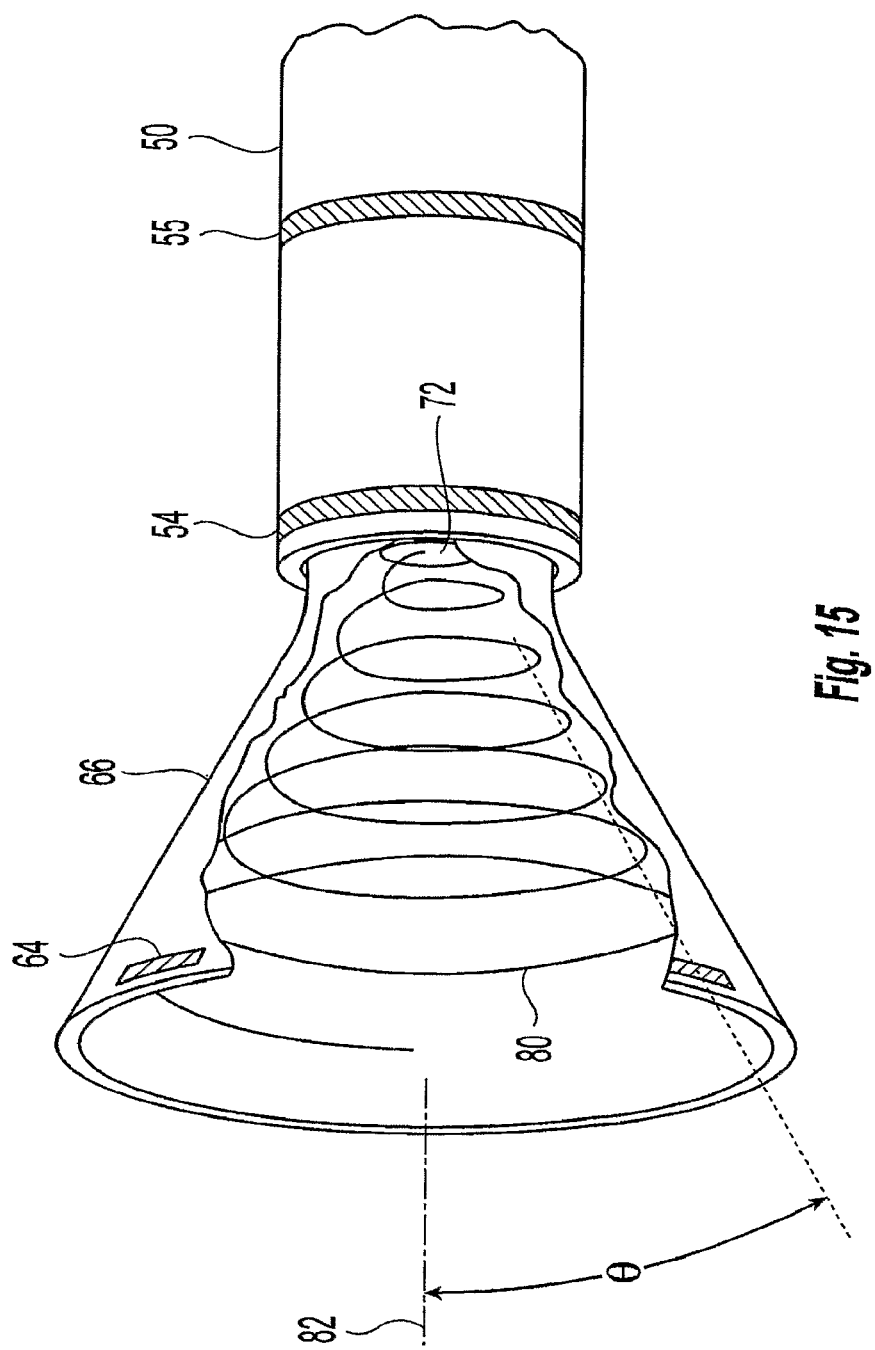
FIG. 15 illustrates an alternative embodiment of the filter extraction system.

The embodiments illustrated in FIGS. 13-18 may utilize a catheter 50 and elongated tubular member 60 similar to those used with other embodiments. In embodiments employing an elongated tubular member 60, the helical extraction wire 80 may be contained within the conical portion 66, as illustrated in FIG. 15. In this configuration, the conical portion 66 will prevent the helical extraction wire 80 from scratching or digging into the walls of the blood vessel. Also, the conical portion 66 and the helical extraction wire 80 may work in combination to position the filter near the centerline 82. Consequently, the conical angle θ of the helical extraction wire 80 may be narrow (such as between approximately parallel to the centerline to approximately 30 degrees) since the conical portion 66 will direct the filter and extraction wire towards each other to facilitate engaging the filter members. In the preferred embodiment, the wire 80 utilizes an atraumatic tip (e.g., a rounded loop, soft tip, cone or sphere).

Figure 16:
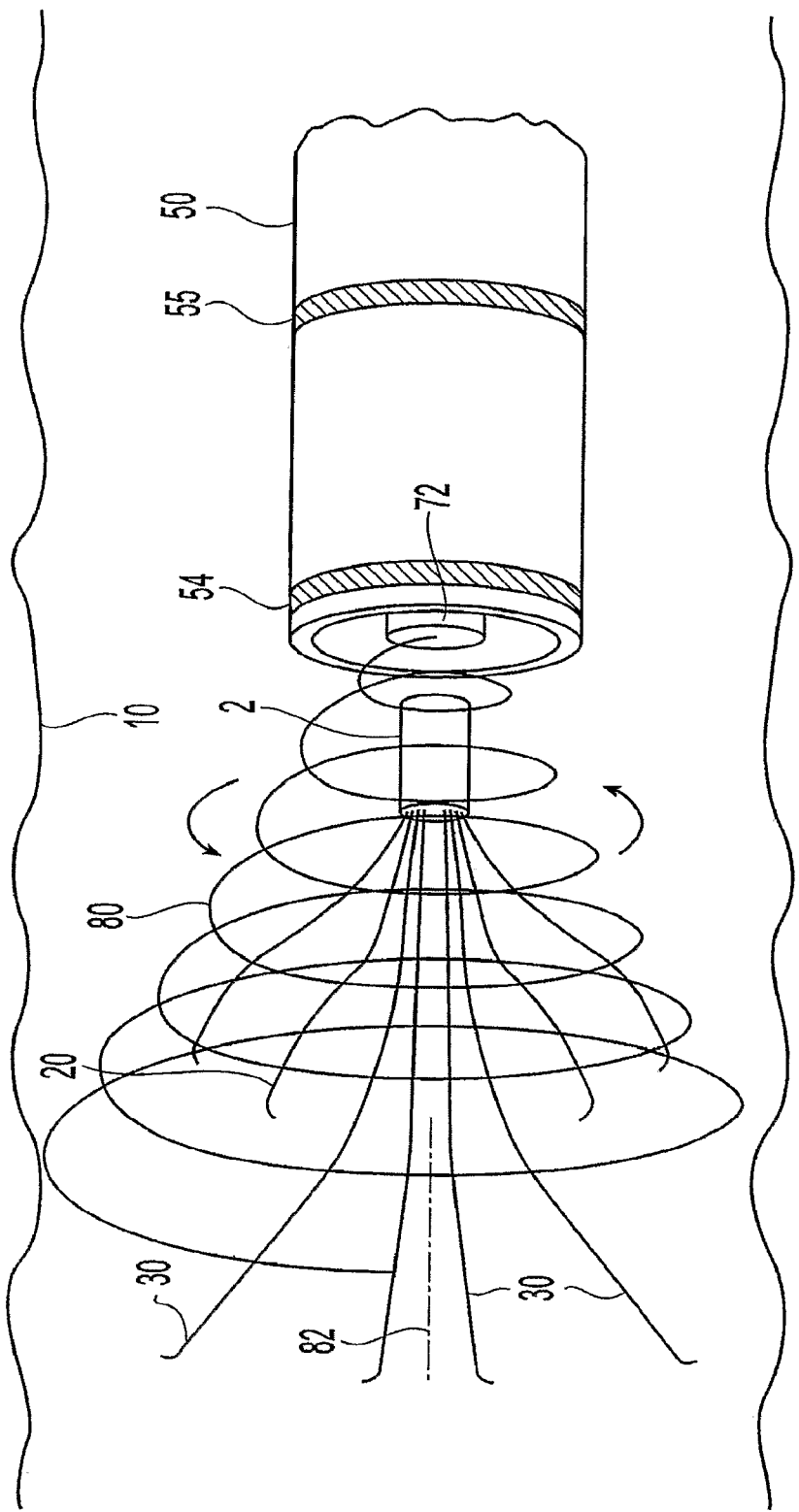
FIG. 16 illustrates a step in the process of extracting a blood filter from a blood vessel according to the extraction system embodiment illustrated in FIG. 13.
Figure 17:
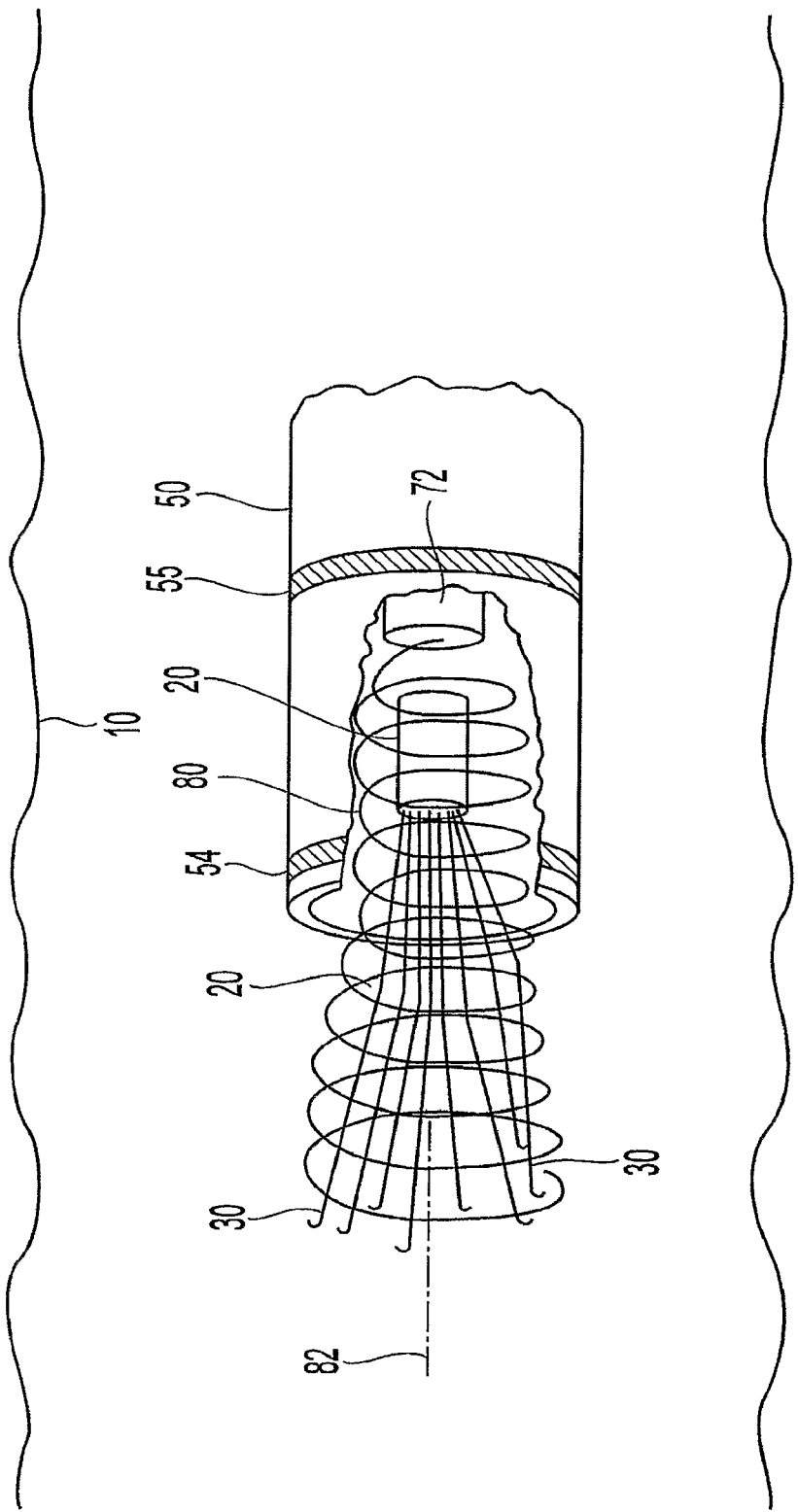
FIG. 17 illustrates a subsequent step in the process of retracting a blood filter from a blood vessel according to the extraction system embodiment illustrated in FIG. 13.
Figure 18:
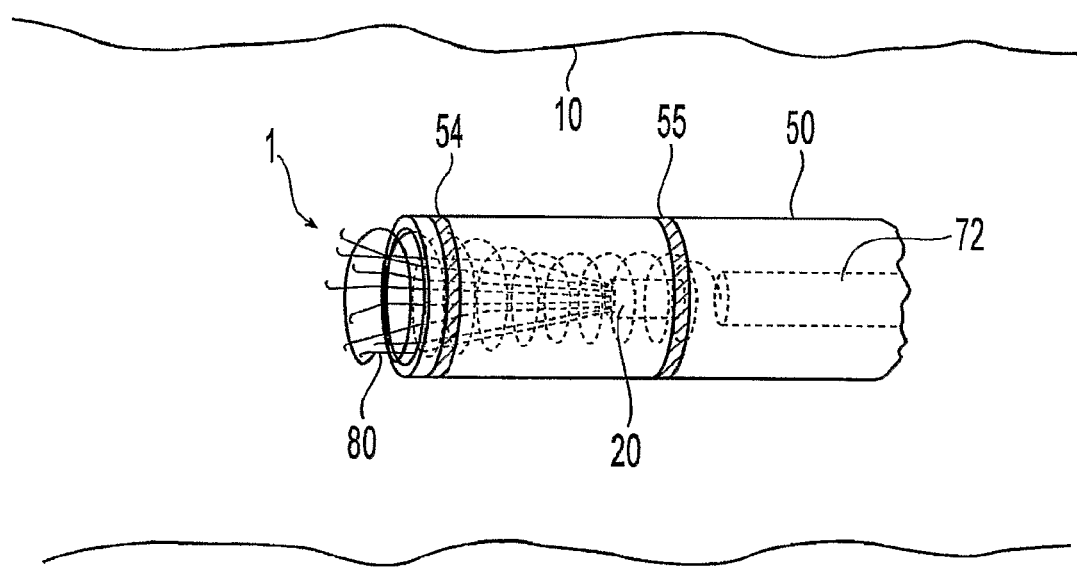
FIG. 18 illustrates a further step in the process of retracting a blood filter from a blood vessel according to the extraction system embodiment illustrated in FIG. 13.

In an alternative embodiment, the conical form of the helical extraction wires 80 may permit eliminating the elongated tubular member 60 since the conical form of the wires may perform the filter locating function otherwise performed by the conical portion 66. Further, as the conical helix 80 is rotated, the wires may draw the filter toward the hub 72 and the filter members 20, 30 toward the centerline. In order to reveal the functioning of the helical extraction wire 80 this embodiment is illustrated in FIGS. 16-18.

In use, the catheter 50 is positioned near the filter 1 within a blood vessel 10, as illustrated in FIG. 8, and the extraction member 70 is advanced in a distal direction until the helical extraction wire 80 is clear of the distal end of the catheter 50. The extraction member 70 may be advanced to pass the helical extraction wire 80 at least partially over the filter, as illustrated in FIG. 16. In this configuration, the clinician rotates the extraction member 70 by rotating a handle on the proximal end. Rotational motion causes the helical extraction wire 80 to pass through the locator members 20 and anchor members 30, pulling the filter members and the wire 80 in toward the centerline 82, as illustrated in FIG. 17. Moving the anchor members 30 toward the centerline causes their hooks to become disengaged from the vessel walls 10 without tearing the endothelial layers, including the endothelial overgrowth. Once the anchor members 30 have been pulled away from the vessel walls, the filter may be drawn into the catheter 50, as illustrated in FIG. 18, by either advancing the catheter in the distal direction while holding the extraction member 70 in a fixed position, or pulling the extraction member 70 in the proximal direction while holding the catheter steady. Once the filter is pulled within the catheter, the catheter may be withdrawn from the patient. Alternatively, the extraction member 70 is not rotated, but instead translated so that the member 70 encircles a substantial portion of the filter. Extraction of the filter can be obtained by moving the catheter 50 and member 70 relative to each other. For example, the catheter 50 may be moved distally away from the clinician while maintaining the extraction member 70 generally stationary; the extraction member 70 and catheter 50 may be moved toward each other; or the extraction member 70 may be moved proximally while maintaining the catheter 50 stationary. Additionally, the helical member can be formed so that its austenite transformation finish temperature Af is greater than 37 degrees Celsius and preferably greater than 42 degrees Celsius so that warm saline (e.g., at greater than 37 degrees Celsius) can be utilized to clamp the helical member down on the filter once the helical member is in position proximate the filter.

Figure 19A:
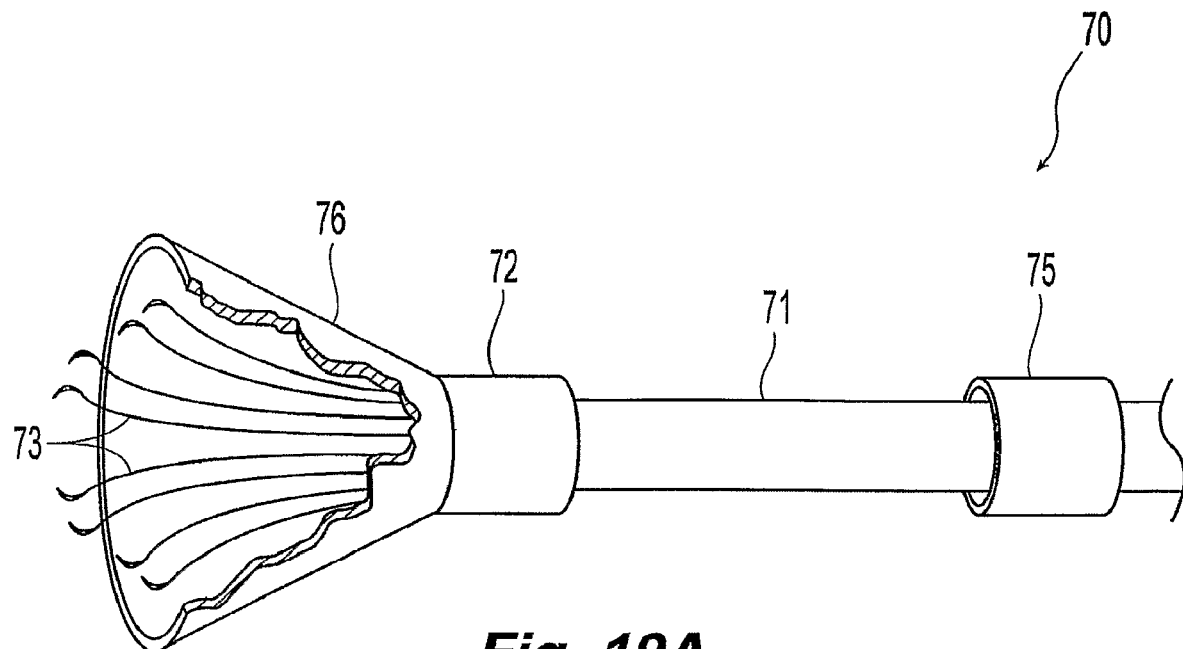
FIGS. 19A and 19B illustrate alternative embodiments of the filter extraction member.
Figure 19B:
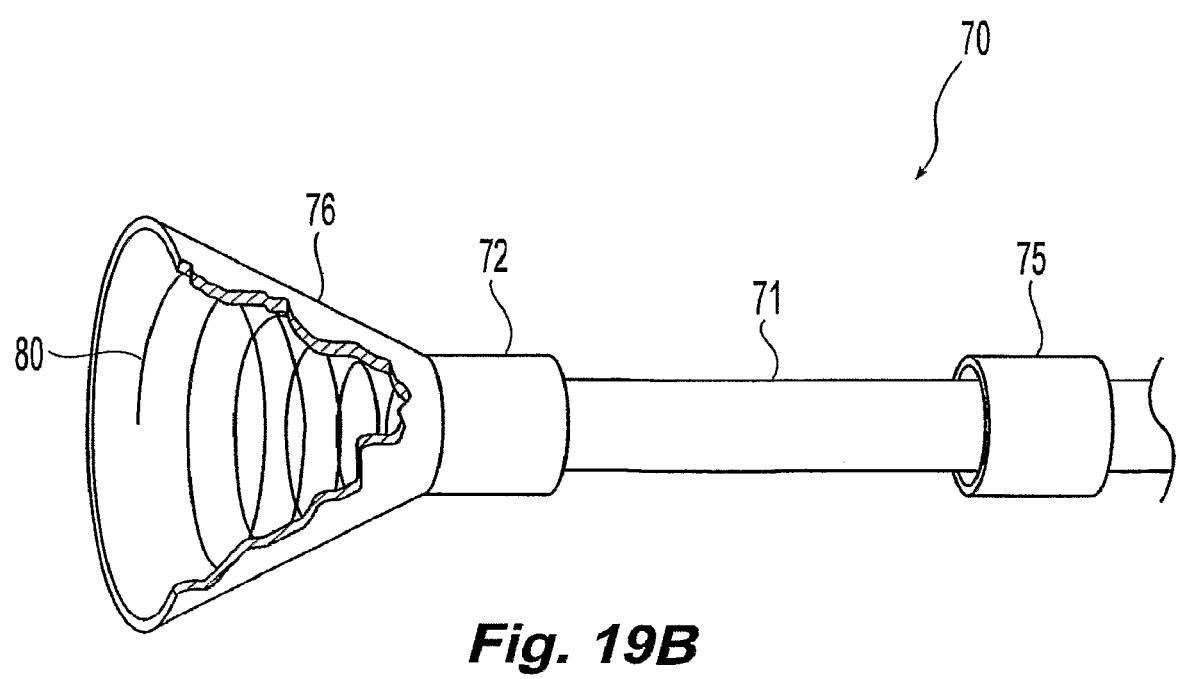

In alternative embodiments illustrated in FIGS. 19A and 19B, the elongated tubular member 60 may be eliminated by coupling a flexible conical portion 76 to the extraction member 70, such as at the distal hub or node 72. In this embodiment, the conical portion 76 may be made of a flexible polymer material, such as polyurethane, polyethylene, polyamide, polyether block amide (PEBA), nylon, and combinations thereof, and coupled to the hub 72 by a bio-compatible adhesive, e.g., cyanoacrylates. The conical portion 76 may include folds or thinned sections (such as, for example, folds 68 illustrated in FIG. 3) to permit the cone to be collapsed in order to fit into a catheter. In use, the conical portion 76 may be deployed by holding the catheter in a fixed position while pushing on the proximal end of the extraction member 70 until the distal end extends from the catheter. Once deployed from the catheter the conical portion 76 is pushed over the filter so the plurality of wires 73 or the helical extraction wire 80 engage the filter members 20, 30. By rotating the extraction member 70, the filter members may be pulled away from the vessel walls. At this point, the conical portion 76 may be used to encircle the filter by pushing the catheter over the filter without moving the extraction member 70 in a manner similar to the methods of use described above.

Several design features are believed to be important in advancing the state of the art. For example, the use of extraction wires 73, 80 to engage the filter members enables pulling the filter anchor members 30 away from the vessel wall 10 before moving the filter. This is believed to help engage the filter hub 2 with the retrieving cone. Also, the use of extraction wires 73; 80 to engage the filter member enables safe removal of a filter that is not configured (e.g., with a removal hook) to be removable. Also, the use of an extraction member with extraction wires 73, 80 to engage the filter members enables a clinician to securely latch onto the filter before the conical portion 66, 76 is collapsed over the filter and is retracted into the catheter. Also, the use of an extraction member 70 that is separate from the elongated tubular member 60 permits the clinician to manipulate the filter grappling wires 73, 80 separately from the conical portion 66 of the tubular member 60. Further, the use of the couplers (e.g., hooks, spheres, loops) allow for locating of the filter in the volume defined by the retrieval cone so that the cone can be utilized to collapse the filter into a smaller configuration suitable for retrieval.

Although the preferred embodiments have been shown and described in relation to the filter of FIG. 1, other filters can also be utilized in conjunction with the removal system described herein as long as these filters are collapsible to a smaller radial configuration. For example, the removal system may be provided for the filter shown and described in U.S. Pat. No. 4,425,908, which is hereby incorporated by reference in its entirety. The system may also be provided for the filter shown and described in U.S. Pat. No. 6,443,972, which is also hereby incorporated by reference in its entirety. Commercially available filters that are collapsible may also be utilized with the filter removal system described. These commercially available filters include but are not limited to the Greenfield® Filter, VenaTech® Filter, Gunther Tulip® Filter, TrapEase® or OptEase®.

While the present invention has been disclosed with reference to certain preferred embodiments, numerous modifications, alterations, and changes to the described embodiments are possible without departing from the sphere and scope of the present invention. Accordingly, it is intended that the present invention not be limited to the described embodiments, but that it has the full scope defined by the language of the following claims, and equivalents thereof.

What is claimed is:

1. A vascular implant and removal apparatus for removing a vascular implant from a vessel wall comprising:
   a) a vascular implant having an outer portion that is adapted to be secured to a blood vessel wall, said implant having a central, longitudinal axis;
   b) a catheter having a diameter and a catheter lumen defining a catheter longitudinal axis;
   c) an elongated extraction device configured to be positioned within the catheter lumen and to move longitudinally and rotationally with respect to the catheter, said extraction device having a tubular member and a rod with a distal end;
   d) the extraction device including at least one helical extraction wire coupled to the distal end of the rod, the at least one helical extraction wire configured as a generally conically shaped helix having a narrow end and a wider end with a first diameter, at least one helical extraction wire coupled to the distal end of the rod at the narrow end;
   e) wherein in an initial vascular implant removal position the wider end of the helical extraction wire engages the vascular implant outer portion, wherein in a final vascular implant removal position the helical extraction wire collapses the outer portion to a second diameter that is smaller than the said first diameter, wherein movement of the vascular implant from the initial removal position to the final removal position is effected by rotation of the extraction device rod and helical extraction wire connected to the vascular implant outer portion;
   f) wherein in the initial removal position, the helical extraction wire first diameter is greater than the diameter of the catheter and less than the diameter of the vessel; and
   g) wherein said final removal position disengages the vascular implant outer portion from the vessel wall by collapsing the outer portion toward said central longitudinal axis.

2. The apparatus of claim 1, wherein said helical extraction wire includes a second extraction wire coupled to the distal end of the elongated extraction device.

3. The apparatus of claim 2, wherein the first and second extraction wires are coaxial with respect to the central, longitudinal axis and rotationally displaced one from the other around the central longitudinal axis.

4. The apparatus of claim 1, further comprising an elongated tubular member having a lumen throughout and a distal end comprising a conical member, wherein the extraction device is positioned within the lumen of the elongated tubular member and wherein at least one helical extraction wire is positioned within the conical member.

5. The apparatus of claim 4, further comprising the conical member being a conical member coupled to the distal end of the extraction device, the conical member configured to surround at least a portion of the at least one helical extraction wire.

6. The apparatus of claim 5, wherein the conical member has a longitudinal axis and the rod has a longitudinal axis, and the longitudinal axis of the conical member is coincident with the longitudinal axis of the rod.

7. The apparatus of claim 4, wherein the helical extraction wire is configured as a helix having a narrow end and a wider end, and the helical extraction wire is coupled to the distal end of the rod at the narrow end.

8. A vascular implant and removal apparatus for removing a vascular implant from a vessel wall comprising:
   a) a vascular implant having a deployed position wherein it is secured to a blood vessel wall, wherein in said deployed position, the implant having an outer portion configured to engage a vessel wall;
   b) an elongated tubular member having a wall with an outer surface and an inner surface, the wall surrounding a lumen, a distal end portion of the tubular member being a conical member;
   c) an elongated extraction member having a proximal end portion and a distal end portion, said extraction member having an outer surface and configured to be positioned within the lumen of the elongated tubular member wherein the outer surface of the extraction member faces the inner surface of the tubular member, the extraction member including a helical wire and configured to move longitudinally and rotationally with respect to the elongated tubular member including a stored position wherein said helical wire is stored within the lumen of the elongated tubular member;
   d) the extraction member and vascular implant defining an initial implant removal position wherein the extraction member engages said outer portion;
   e) wherein a rotation of the extraction member and helical wire effects movement of the implant from the initial implant removal position to a final implant removal position;
   f) a catheter having a lumen and an inner surface that contains and closely conforms to the tubular member, the tubular member being movable relative to the catheter and wherein the catheter inner surface is abutting the outer surface of the tubular member wall;
   g) wherein a storage position is defined by the conical member collapsing as the catheter pushes over the conical member to fit within the catheter lumen; and
   h) wherein the conical member expands when extended outside the catheter lumen.

9. The apparatus of claim 8, further comprising a handle coupled to a proximal end of said extraction member, the elongated tubular member configured to be inserted into and moved longitudinally within the catheter lumen.

10. The apparatus of claim 9, wherein the conical member has a radio-opaque marker.

11. The apparatus of claim 8, wherein the extraction member comprises a radio-opaque marker.

12. The apparatus of claim 8, wherein the tubular member further comprises a handle coupled to a proximal end, the tubular member handle configured to permit insertion and withdrawal of the tubular member in the catheter without moving the catheter.

13. The apparatus of claim 8, wherein the extraction member further comprises a handle on a proximal end, the extraction member handle configured to permit inserting and withdrawing the extraction member within the tubular member without moving the tubular member or the catheter.

14. The apparatus of claim 8, wherein the conical member of the tubular member comprises a radio-opaque marker.

15. The apparatus of claim 8, wherein a distal end of the catheter comprises a radio-opaque marker.

* * * * *